(12) United States Patent
Kahook et al.

(10) Patent No.: US 9,387,069 B2
(45) Date of Patent: Jul. 12, 2016

(54) MODULAR INTRAOCULAR LENS DESIGNS AND METHODS

(71) Applicants: The Regents of the University of Colorado, a body corporate, Denver, CO (US); ClarVista Medical, Inc., Aliso Viejo, CA (US)

(72) Inventors: Malik Y. Kahook, Denver, CO (US); Naresh Mandava, Denver, CO (US); Paul McLean, North Oaks, MN (US); Robert E. Atkinson, Lake Elmo, MN (US)

(73) Assignees: ClarViata Medical, Inc., Aliso Viejo, CA (US); The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/808,022

(22) Filed: Jul. 24, 2015

(65) Prior Publication Data

US 2015/0342729 A1     Dec. 3, 2015

Related U.S. Application Data

(60) Continuation of application No. 13/937,761, filed on Jul. 9, 2013, now Pat. No. 9,125,736, which is a (Continued)

(51) Int. Cl.
*A61F 2/16* (2006.01)

(52) U.S. Cl.
CPC ............... *A61F 2/1613* (2013.01); *A61F 2/16* (2013.01); *A61F 2/1648* (2013.01); *A61F 2002/169* (2015.04); *A61F 2002/1689* (2013.01); *A61F 2002/16902* (2015.04)

(58) Field of Classification Search
CPC ..... A61F 2/1662; A61F 2/1667; A61F 2/167; A61F 2/1648; A61F 2/1664; A61F 2/1672; A61F 2/1675; A61F 2/1678; A61F 2/1613; A61F 2/1624; A61F 2/1637
See application file for complete search history.

(56) References Cited

U.S. PATENT DOCUMENTS

| 4,168,547 A | 9/1979 | Konstantinov et al. |
| 4,409,691 A | 10/1983 | Levy |

(Continued)

FOREIGN PATENT DOCUMENTS

| EP | 1 138 282 A1 | 10/2001 |
| EP | 1 296 616 B1 | 5/2012 |

(Continued)

OTHER PUBLICATIONS

PCT International Search Report and Written Opinion for International Application No. PCT/US2013/022752 mailed Apr. 19, 2013 (10 pages).

(Continued)

*Primary Examiner* — Howie Matthews
(74) *Attorney, Agent, or Firm* — Bookoff McAndrews, PLLC

(57) ABSTRACT

A modular IOL system including intraocular primary and secondary components, which, when combined, form an intraocular optical correction device, wherein the secondary component is placed on the primary component within the perimeter of the capsulorhexis, thus avoiding the need to touch or otherwise manipulate the capsular bag. The secondary component may be manipulated, removed, and/or exchanged for a different secondary component for correction or modification of the optical result, on an intra-operative or post-operative basis, without the need to remove the primary component and without the need to manipulate the capsular bag. The primary component may have haptics extending therefrom for centration in the capsular bag, and the secondary component may exclude haptics, relying instead on attachment to the primary lens for stability. Such attachment may reside radially inside the perimeter of the capsulorhexis and radially outside the field of view to avoid interference with light transmission.

28 Claims, 24 Drawing Sheets

Related U.S. Application Data division of application No. 13/748,207, filed on Jan. 23, 2013, now Pat. No. 9,095,424.

(60) Provisional application No. 61/589,981, filed on Jan. 24, 2012, provisional application No. 61/677,213, filed on Jul. 30, 2012.

(56) References Cited

U.S. PATENT DOCUMENTS

| | | |
|---|---|---|
| 4,435,856 A | 3/1984 | L'Esperance |
| 4,741,330 A | 5/1988 | Hayhurst |
| 4,769,035 A | 9/1988 | Kelman |
| 4,816,031 A | 3/1989 | Pfoff |
| 4,828,558 A | 5/1989 | Kelman |
| 4,842,601 A | 6/1989 | Smith |
| 4,932,971 A | 6/1990 | Kelman |
| 4,960,418 A | 10/1990 | Tennant |
| 5,026,396 A | 6/1991 | Darin |
| 5,098,444 A | 3/1992 | Feaster |
| 5,133,747 A | 7/1992 | Feaster |
| 5,147,369 A | 9/1992 | Wagner |
| 5,152,788 A | 10/1992 | Isaacson et al. |
| 5,201,762 A | 4/1993 | Hauber |
| 5,222,981 A | 6/1993 | Werblin |
| 5,354,335 A | 10/1994 | Lipshitz et al. |
| 5,358,520 A | 10/1994 | Patel |
| 5,366,502 A | 11/1994 | Patel |
| 5,391,202 A | 2/1995 | Lipshitz et al. |
| 5,410,375 A | 4/1995 | Fiala |
| 5,417,369 A | 5/1995 | Lipson |
| 5,507,805 A | 4/1996 | Koeniger |
| 5,578,081 A | 11/1996 | McDonald |
| 5,628,795 A | 5/1997 | Langerman |
| 5,728,155 A | 3/1998 | Anello et al. |
| 5,769,890 A | 6/1998 | McDonald |
| 5,814,103 A | 9/1998 | Lipshitz et al. |
| 5,824,074 A | 10/1998 | Koch |
| 5,860,985 A | 1/1999 | Anschutz |
| 5,876,442 A | 3/1999 | Lipshitz et al. |
| 5,895,422 A | 4/1999 | Hauber |
| 5,928,283 A | 7/1999 | Gross et al. |
| 5,964,802 A | 10/1999 | Anello et al. |
| 5,968,094 A | 10/1999 | Werblin et al. |
| 6,027,531 A | 2/2000 | Tassignon |
| 6,066,171 A | 5/2000 | Lipshitz et al. |
| 6,113,633 A | 9/2000 | Portney |
| 6,197,057 B1 | 3/2001 | Peyman et al. |
| 6,197,058 B1 | 3/2001 | Portney |
| 6,228,113 B1 | 5/2001 | Kaufman |
| 6,231,603 B1 | 5/2001 | Lang et al. |
| 6,277,146 B1 | 8/2001 | Peyman et al. |
| 6,280,471 B1 | 8/2001 | Peyman et al. |
| 6,358,280 B1 | 3/2002 | Herrick |
| 6,413,276 B1 | 7/2002 | Werblin |
| 6,423,094 B1 | 7/2002 | Sarfarazi |
| 6,454,801 B1 | 9/2002 | Portney |
| 6,464,725 B2 | 10/2002 | Skotton |
| 6,488,708 B2 | 12/2002 | Sarfarazi |
| 6,537,281 B1 | 3/2003 | Portney |
| 6,551,354 B1 | 4/2003 | Ghazizadeh et al. |
| 6,554,859 B1 | 4/2003 | Lang et al. |
| 6,558,420 B2 | 5/2003 | Green |
| 6,596,026 B1 | 7/2003 | Gross et al. |
| 6,599,317 B1 | 7/2003 | Weinschenk, III et al. |
| 6,616,692 B1 | 9/2003 | Glick et al. |
| 6,638,304 B2 | 10/2003 | Azar |
| 6,695,881 B2 | 2/2004 | Peng et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,846,326 B2 | 1/2005 | Zadno-Azizi et al. |
| 6,858,040 B2 | 2/2005 | Nguyen et al. |
| 6,899,732 B2 | 5/2005 | Zadno-Azizi et al. |
| 6,926,736 B2 | 8/2005 | Peng et al. |
| 6,960,231 B2 | 11/2005 | Tran |
| 6,969,403 B2 | 11/2005 | Peng et al. |
| 6,972,032 B2 | 12/2005 | Aharoni et al. |
| 6,972,034 B2 | 12/2005 | Tran et al. |
| 6,991,651 B2 | 1/2006 | Portney |
| 7,008,447 B2 | 3/2006 | Koziol |
| 7,041,134 B2 | 5/2006 | Nguyen et al. |
| 7,081,134 B2 | 7/2006 | Cukrowski |
| 7,087,080 B2 | 8/2006 | Zadno-Azizi et al. |
| 7,097,660 B2 | 8/2006 | Portney |
| 7,101,397 B2 | 9/2006 | Aharoni |
| 7,118,596 B2 | 10/2006 | Zadno-Azizi et al. |
| 7,122,053 B2 | 10/2006 | Esch |
| 7,125,422 B2 | 10/2006 | Woods et al. |
| 7,186,266 B2 | 3/2007 | Peyman |
| 7,198,640 B2 | 4/2007 | Nguyen |
| 7,220,278 B2 | 5/2007 | Peyman |
| 7,223,288 B2 | 5/2007 | Zhang et al. |
| 7,226,478 B2 | 6/2007 | Ting et al. |
| 7,238,201 B2 | 7/2007 | Portney et al. |
| 7,300,464 B2 | 11/2007 | Tran |
| 7,316,713 B2 | 1/2008 | Zhang |
| 7,452,378 B2 | 11/2008 | Zadno-Azizi et al. |
| 7,582,113 B2 | 9/2009 | Terwee |
| 7,591,849 B2 | 9/2009 | Richardson |
| 7,645,299 B2 | 1/2010 | Koziol |
| 7,662,179 B2 | 2/2010 | Sarfarazi |
| 7,727,277 B2 | 6/2010 | Aharoni et al. |
| 7,736,390 B2 | 6/2010 | Aharoni et al. |
| 7,780,729 B2 | 8/2010 | Nguyen et al. |
| 7,811,320 B2 | 10/2010 | Werblin |
| 7,857,850 B2 | 12/2010 | Mentak et al. |
| 7,871,437 B2 | 1/2011 | Hermans et al. |
| 7,918,886 B2 | 4/2011 | Aharoni et al. |
| 7,985,253 B2 | 7/2011 | Cumming |
| 7,993,399 B2 | 8/2011 | Peyman |
| 7,998,198 B2 | 8/2011 | Angelopoulos et al. |
| 8,012,204 B2 | 9/2011 | Weinschenk, III et al. |
| 8,034,106 B2 | 10/2011 | Mentak et al. |
| 8,034,107 B2 | 10/2011 | Stenger |
| 8,034,108 B2 | 10/2011 | Bumbalough |
| 8,062,361 B2 | 11/2011 | Nguyen et al. |
| 8,066,768 B2 | 11/2011 | Werblin |
| 8,066,769 B2 | 11/2011 | Werblin |
| 8,128,693 B2 | 3/2012 | Tran et al. |
| 8,137,399 B2 | 3/2012 | Glazier et al. |
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,197,541 B2 | 6/2012 | Schedler |
| 8,273,123 B2 | 9/2012 | Ben Nun |
| 8,287,593 B2 | 10/2012 | Portney |
| 8,377,124 B2 | 2/2013 | Hong et al. |
| 8,425,597 B2 | 4/2013 | Glick et al. |
| 8,663,235 B2 | 3/2014 | Tassignon |
| 8,728,158 B2 | 5/2014 | Whitsett |
| 8,758,434 B2 | 6/2014 | Scott |
| 2003/0144733 A1 | 7/2003 | Brady et al. |
| 2003/0158560 A1 | 8/2003 | Portney |
| 2004/0010310 A1 | 1/2004 | Peyman |
| 2004/0148022 A1 | 7/2004 | Eggleston |
| 2004/0236422 A1 | 11/2004 | Zhang et al. |
| 2004/0243142 A1 | 12/2004 | Siepser |
| 2005/0027354 A1 | 2/2005 | Brady et al. |
| 2006/0111776 A1 | 5/2006 | Glick et al. |
| 2007/0123981 A1 | 5/2007 | Tassignon |
| 2008/0046077 A1 | 2/2008 | Cumming |
| 2008/0103592 A1 | 5/2008 | Maloney |
| 2009/0005864 A1 | 1/2009 | Eggleston |
| 2011/0040378 A1 | 2/2011 | Werblin |
| 2011/0251686 A1 | 10/2011 | Masket |
| 2012/0179249 A1 | 7/2012 | Coleman |
| 2013/0184815 A1 | 7/2013 | Roholt |
| 2013/0190868 A1 | 7/2013 | Kahook et al. |
| 2014/0052246 A1 | 2/2014 | Kahook et al. |
| 2014/0371852 A1 | 12/2014 | Aharoni et al. |

(56) References Cited

U.S. PATENT DOCUMENTS

FOREIGN PATENT DOCUMENTS

| | | | |
|---|---|---|---|
| JP | 5705529 | B2 | 4/2015 |
| WO | WO 03/039335 | A2 | 5/2003 |
| WO | WO 2008/094518 | A1 | 8/2008 |
| WO | WO 2010/002215 | A2 | 1/2010 |
| WO | WO 2013/112589 | A1 | 8/2013 |
| WO | WO 2013/158942 | A1 | 10/2013 |
| WO | WO 2014/197170 | A1 | 12/2014 |

OTHER PUBLICATIONS

PCT International Search Report and Written Opinion for International Application No. PCT/US2014/037646 mailed Aug. 18, 2014 (14 pages).

ETCHED GROOVE

FIG. 14
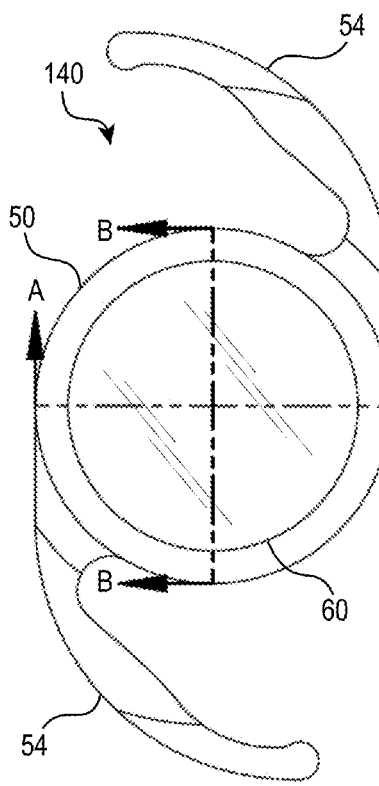
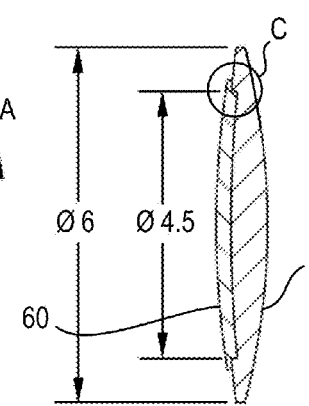
FIG. 14B
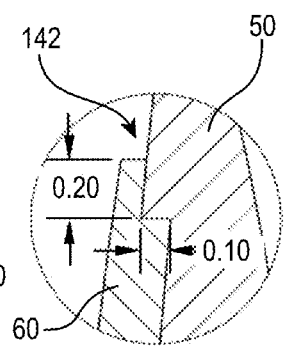
FIG. 14C
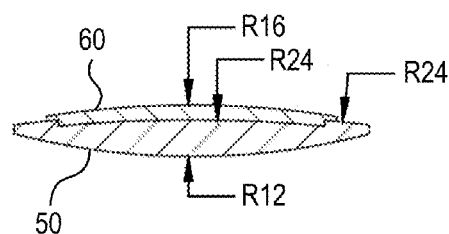
FIG. 14A

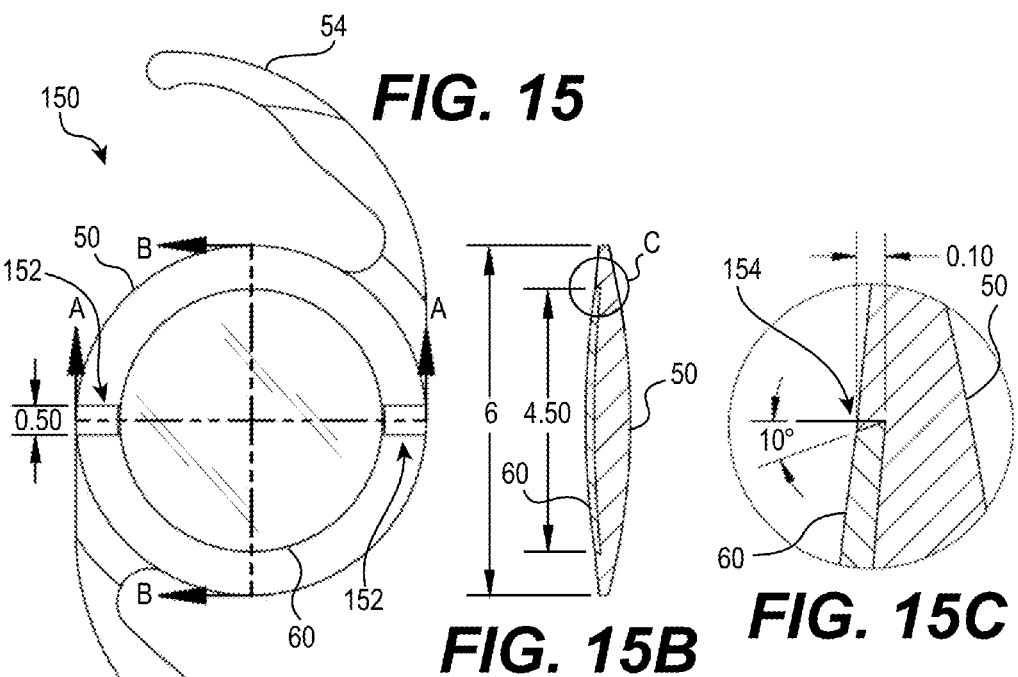
FIG. 15
FIG. 15B
FIG. 15C
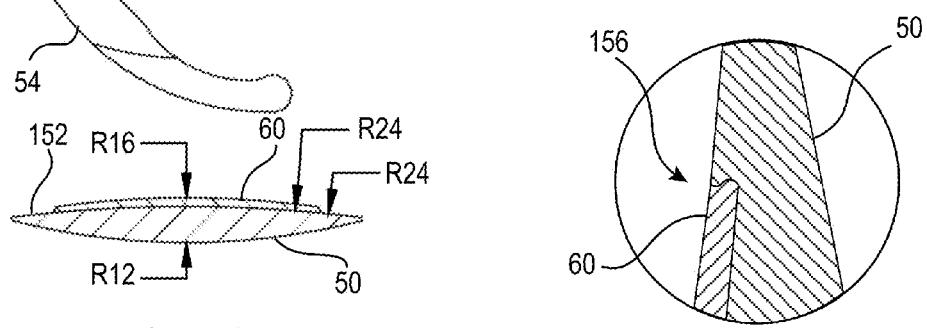
FIG. 15A
FIG. 15D

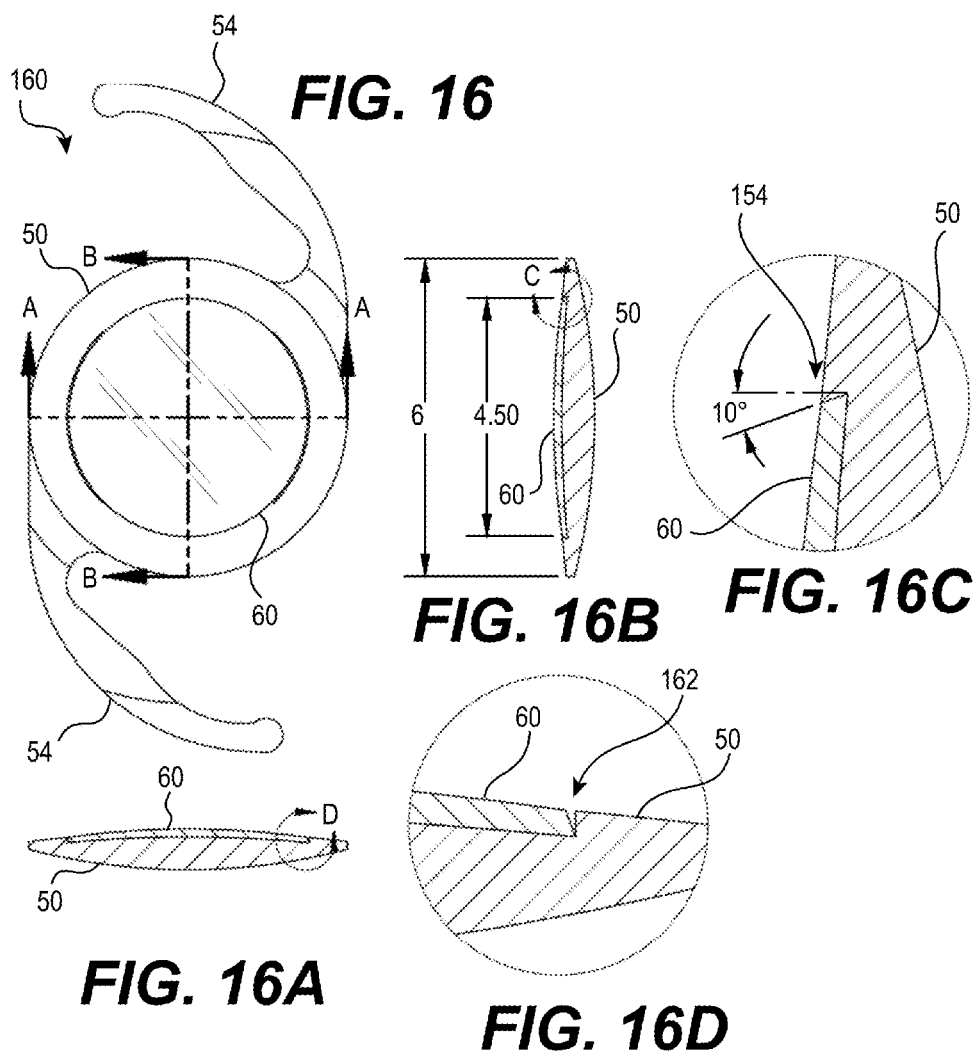

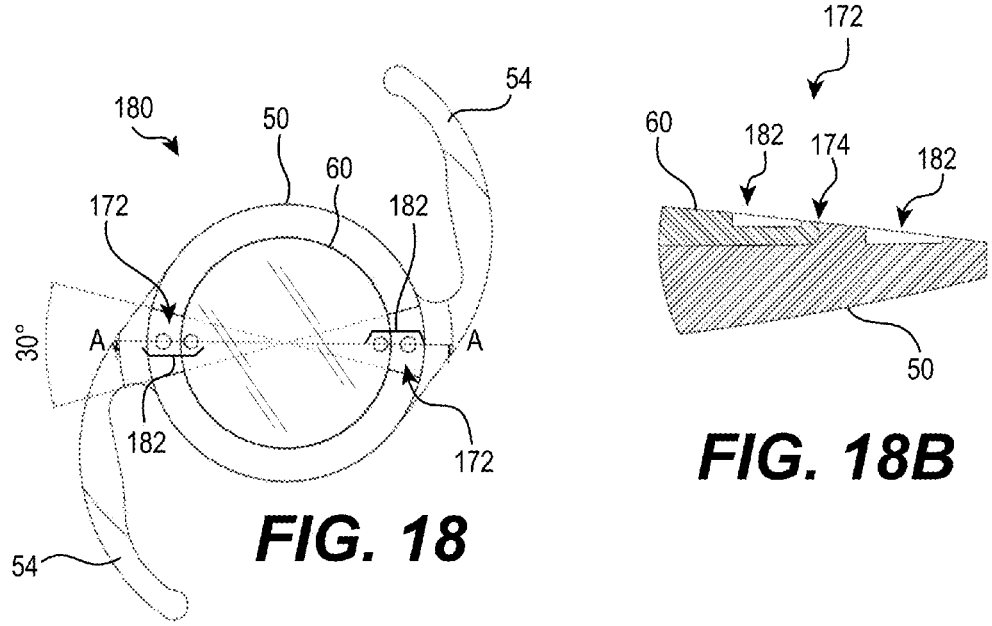
FIG. 18
FIG. 18B
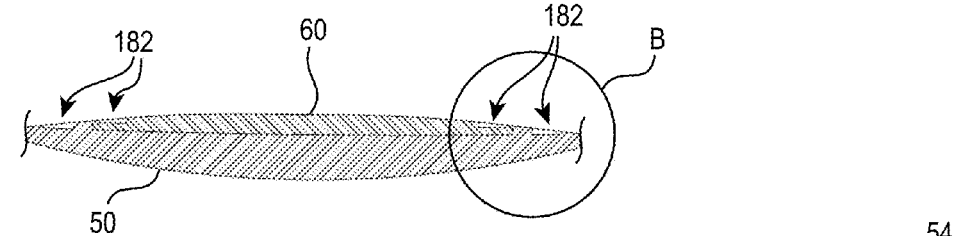
FIG. 18A
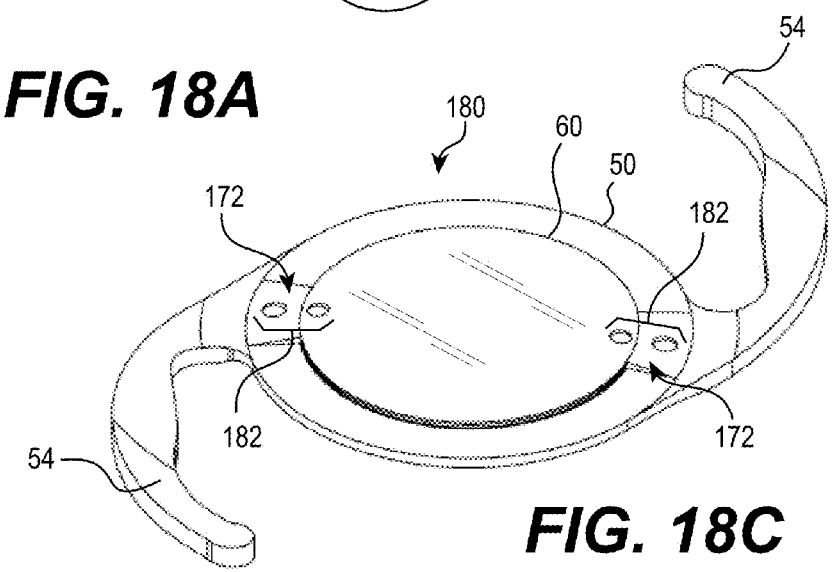
FIG. 18C

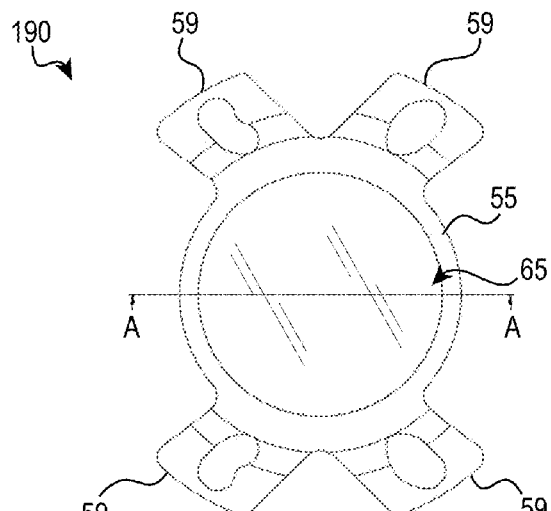
FIG. 19
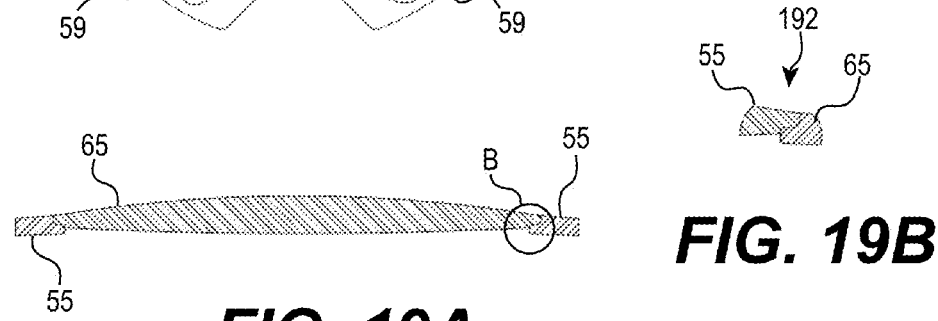
FIG. 19B
FIG. 19A
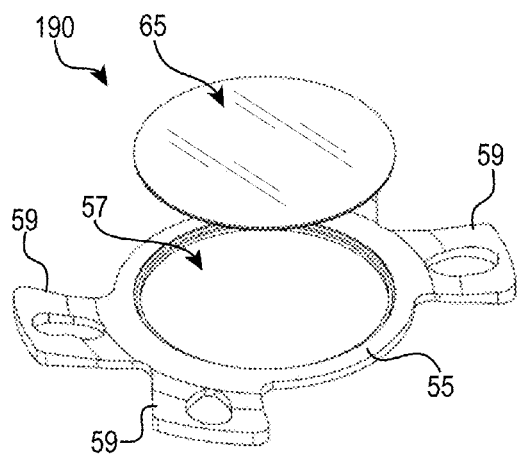 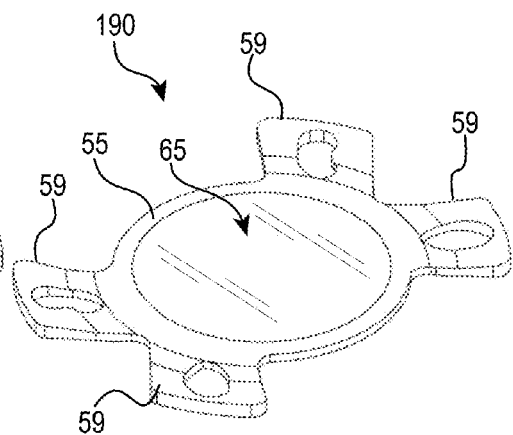
FIG. 19C      FIG. 19D

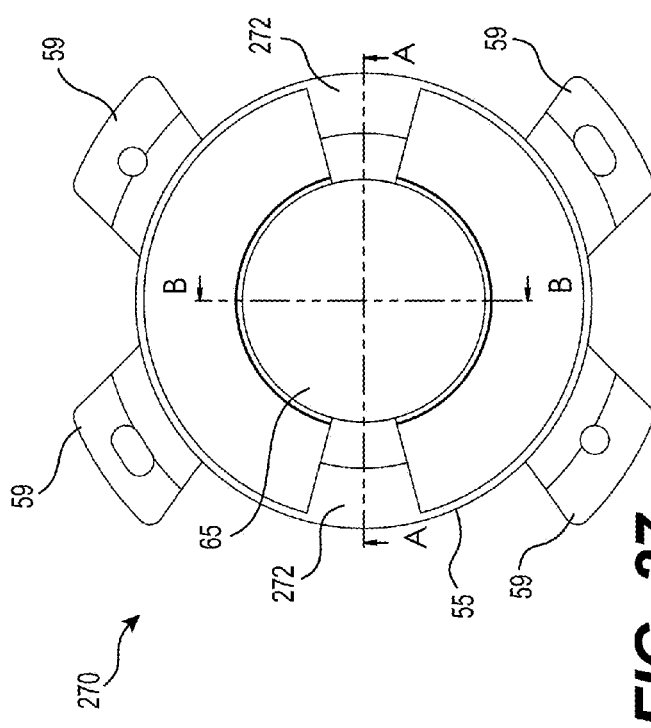
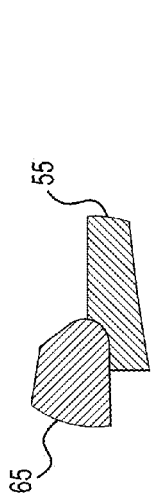
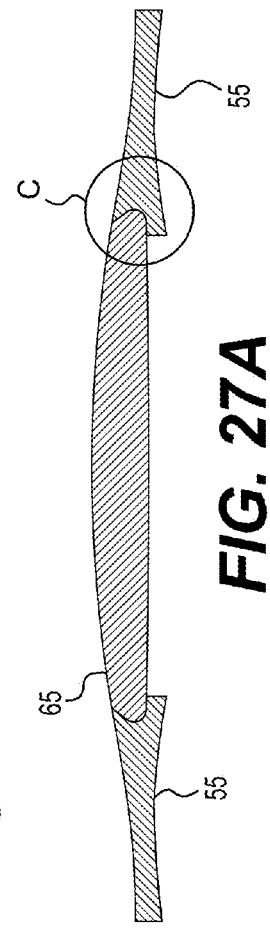
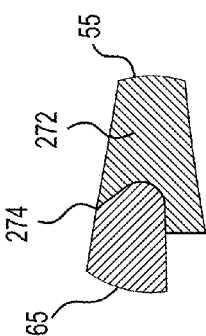

MODULAR INTRAOCULAR LENS DESIGNS AND METHODS

CROSS-REFERENCE TO RELATED APPLICATIONS

This application is a continuation of U.S. application Ser. No. 13/937,761 filed on Jul. 9, 2013, now U.S. Pat. No. 9,125,736, which is a divisional of U.S. application Ser. No. 13/748,207 filed on Jan. 23, 2013, now U.S. Pat. No. 9,095,424, which claims the benefits under 35 U.S.C. §119(e) of priority of U.S. Provisional Patent Application No. 61/589,981 filed on Jan. 24, 2012, entitled "LASER ETCHING OF IN SITU INTRAOCULAR LENS AND SUCCESSIVE SECONDARY LENS IMPLANTATION," and of U.S. Provisional Patent Application No. 61/677,213 filed on Jul. 30, 2012, entitled "MODULAR INTRAOCULAR LENS DESIGNS & METHODS," each of which is incorporated herein by reference.

FIELD OF THE INVENTION

The present disclosure generally relates to embodiments of intraocular lenses (IOLs). More specifically, the present disclosure relates to embodiments of modular IOL designs and methods.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens.

When age or disease causes the lens to become less transparent (e.g., cloudy), vision deteriorates because of the diminished light, which can be transmitted to the retina. This deficiency in the lens of the eye is medically known as a cataract. An accepted treatment for this condition is surgical removal of the lens from the capsular bag and placement of an artificial intraocular lens (IOL) in the capsular bag. In the United States, the majority of cataractous lenses are removed by a surgical technique called phacoemulsification. During this procedure, an opening (capsulorhexis) is made in the anterior side of the capsular bag and a thin phacoemulsification-cutting tip is inserted into the diseased lens and vibrated ultrasonically. The vibrating cutting tip liquefies or emulsifies the lens so that the lens may be aspirated out of the capsular bag. The diseased lens, once removed, is replaced by an IOL.

After cataract surgery to implant an IOL, the optical result may be suboptimal or may need adjustment over time. For example, shortly after the procedure, it may be determined that the refractive correction is erroneous leading to what is sometimes called "refractive surprise." Also for example, long after the procedure, it may be determined that the patient needs or desires a different correction, such as a stronger refractive correction, an astigmatism correction, or a multifocal correction.

In each of these cases, a surgeon may be reluctant to attempt removal of the suboptimal IOL from the capsular bag and replacement with a new IOL. In general, manipulation of the capsular bag to remove an IOL risks damage to the capsular bag including posterior rupture. This risk increases over time as the capsular bag collapses around the IOL and tissue ingrowth surrounds the haptics of the IOL. Thus, it would be desirable to be able to correct or modify the optical result without the need to remove the IOL or manipulate the capsular bag.

A variety of secondary lenses have been proposed to address the aforementioned drawbacks. For example, one possible solution includes a secondary lens that resides anterior to the capsular bag with haptics that engage the ciliary sulcus. While this design may have the advantage of avoiding manipulation of the capsular bag, its primary disadvantage is engaging the ciliary sulcus. The ciliary sulcus is composed of soft vascularized tissue that is susceptible to injury when engaged by haptics or other materials. Such injury may result in complications such as bleeding, inflammation and hyphema. Thus, in general, it may be desirable to avoid placing a secondary lens in the ciliary sulcus to avoid the potential for complications.

Another potential solution may include a lens system that avoids the potential problems associated with the ciliary sulcus. The lens system may include a primary lens and a secondary lens, where the secondary lens may be attached to the primary lens, both within the capsular bag. The primary lens may have a recess into which an edge of the secondary lens may be inserted for attachment. The recess is preferably located radially outwardly of the opening (capsulorhexis) in the capsular bag to avoid interfering with light transmission. To attach the secondary lens in-situ, the capsular bag must be manipulated around the perimeter of the capsulorhexis to gain access to the recess in the primary lens. As stated previously, manipulation of the capsular bag may be undesirable given the risks associated therewith. Therefore, while such lens systems may avoid the potential for injury to the ciliary sulcus by implanting both the primary lens and the secondary lens in the capsular bag, these systems do not avoid manipulation of the capsular bag to attach the secondary lens.

Thus, there remains a need for an IOL system and method that allows for correction or modification of the optical result using a secondary lens that can be attached to a primary lens without the need manipulate the capsular bag.

SUMMARY OF THE INVENTION

Embodiments of the present disclosure provide a modular IOL system including intraocular primary and secondary components, which, when combined, form an intraocular optical correction device. The primary component may comprise an intraocular base, and the secondary component may comprise an intraocular lens, wherein the base is configured to releasably receive the intraocular lens. In some embodiments, the base may be configured as a lens, in which case the modular IOL system may be described as including a primary lens and a secondary lens. The primary component (e.g., base or primary lens) may be placed in the capsular bag using conventional cataract surgery techniques. The primary component may have a diameter greater than the diameter of the capsulorhexis to retain the primary component in the capsular bag. The secondary component (e.g., secondary lens) may have a diameter less than the diameter of the capsulorhexis such that the secondary component may be attached to the primary component without manipulation of the capsular bag. The secondary component may also be manipulated to correct or modify the optical result, intra-operatively or post-operatively, without the need to remove the primary component and without the need to manipulate the capsular bag. For example, the secondary component may be removed, repositioned, and/or exchanged to correct, modify, and/or fine tune the optical result.

Common indications for exchanging the secondary component may be residual refractive error (e.g., for monofocal lenses), decentration error (e.g., for multifocal lenses) due to post-operative healing, astigmatism error (e.g., for toric lenses) induced by surgery, changing optical correction needs due to progressive disease, changing optical correction desires due to lifestyle changes, injury, age, etc.

The primary component may have haptics (e.g., projections) extending therefrom for centration in the capsular bag, and the secondary component may exclude haptics, relying instead on attachment to the primary component for stability. Such attachment may reside radially inside the perimeter of the capsulorhexis and radially outside the field of view to avoid interference with light transmission. Alternatively or in addition, the attachment may comprise a small fraction of the perimeter (e.g., less than 20%) of the secondary component to minimize the potential for interference in light transmission.

The primary component may have an anterior surface that is in intimate contact with a posterior surface of the secondary component to prevent fluid ingress, tissue ingrowth, and/or optical interference. The secondary component may be removably secured to the primary component by mechanical attachment and/or chemical attraction, for example. Mechanical attachment may be facilitated by mating or interlocking geometries corresponding to each of the primary and the secondary components. Such geometries may be preformed by molding or cutting, for example, or formed in-situ by laser etching, for example. Chemical attraction may be facilitated by using similar materials with a smooth surface finish activated by a surface treatment, for example. In some instances, it may be desirable to reduce chemical attraction and rely more on mechanical attachment for stability. In this case, the primary and secondary components may be formed of dissimilar materials or otherwise have adjacent surfaces that do not have a chemical attraction.

The modular IOL systems and methods according to embodiments of the present disclosure may be applied to a variety of IOL types, including fixed monofocal, multifocal, toric, accommodative, and combinations thereof. In addition, the modular IOL systems and methods according to embodiments of the present disclosure may be used to treat, for example: cataracts, large optical errors in myopic (near-sighted), hyperopic (far-sighted), and astigmatic eyes, ectopia lentis, aphakia, pseudophakia, and nuclear sclerosis.

Various other aspects of embodiments of the present disclosure are described in the following detailed description and drawings.

BRIEF DESCRIPTION OF THE DRAWINGS

The drawings illustrate example embodiments of the present disclosure. The drawings are not necessarily to scale, may include similar elements that are numbered the same, and may include dimensions (in millimeters) and angles (in degrees) by way of example, not necessarily limitation. In the drawings:

FIGS. 14, 14A-14C, 15, 15A-15D, 16, 16A-16D, 17, 17A-17C, 18, 18A-18C, 19, 19A-19D, 20, 20A-20I, 21, 21A-E, 22, and 22A-22D are various views of alternative modular IOLs according to embodiments of the present disclosure;

FIGS. 27 and 27A-27D are various views of a further embodiment of a modular IOL, according to the present disclosure.

DETAILED DESCRIPTION

Figure 1:
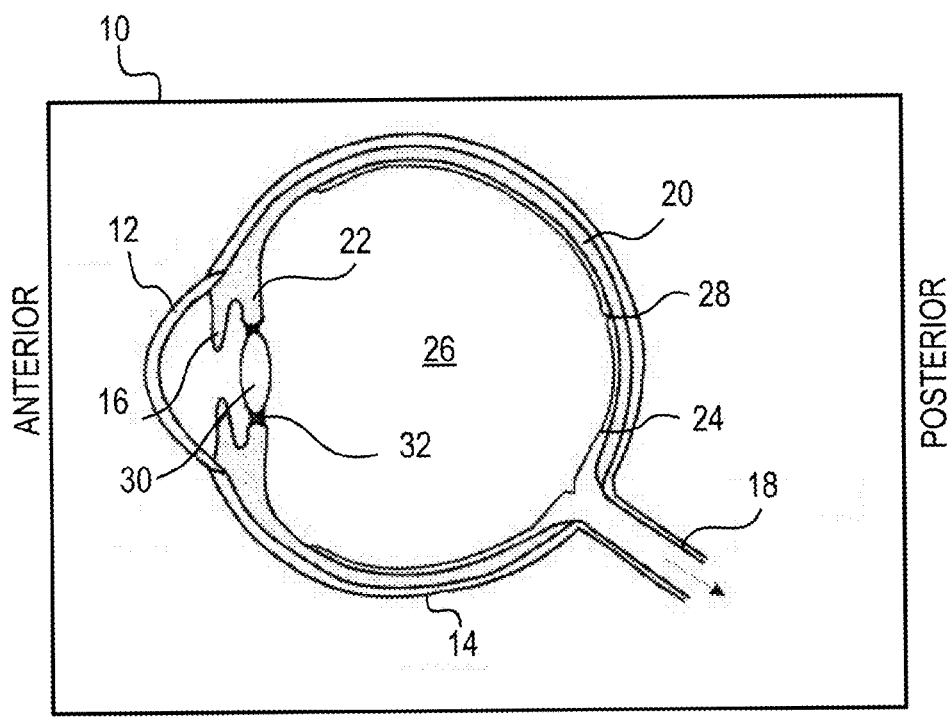
FIG. 1 is a schematic diagram of the human eye shown in cross section.

With reference to FIG. 1, the human eye 10 is shown in cross section. The eye 10 has been described as an organ that reacts to light for several purposes. As a conscious sense organ, the eye allows vision. Rod and cone cells in the retina 24 allow conscious light perception and vision including color differentiation and the perception of depth. In addition, the human eye's non-image-forming photosensitive ganglion cells in the retina 24 receive light signals which affect adjustment of the size of the pupil, regulation and suppression of the hormone melatonin, and entrainment of the body clock.

The eye 10 is not properly a sphere; rather it is a fused two-piece unit. The smaller frontal unit, more curved, called the cornea 12 is linked to the larger unit called the sclera 14. The corneal segment 12 is typically about 8 mm (0.3 in) in radius. The sclera 14 constitutes the remaining five-sixths; its radius is typically about 12 mm. The cornea 12 and sclera 14 are connected by a ring called the limbus. The iris 16, the color of the eye, and its black center, the pupil, are seen instead of the cornea 12 due to the cornea's 12 transparency. To see inside the eye 10, an ophthalmoscope is needed, since light is not reflected out. The fundus (area opposite the pupil), which includes the macula 28, shows the characteristic pale optic disk (papilla), where vessels entering the eye pass across and optic nerve fibers 18 depart the globe.

Thus, the eye 10 is made up of three coats, enclosing three transparent structures. The outermost layer is composed of the cornea 12 and sclera 14. The middle layer consists of the choroid 20, ciliary body 22, and iris 16. The innermost layer is the retina 24, which gets its circulation from the vessels of the choroid 20 as well as the retinal vessels, which can be seen within an ophthalmoscope. Within these coats are the aqueous humor, the vitreous body 26, and the flexible lens 30. The aqueous humor is a clear fluid that is contained in two areas: the anterior chamber between the cornea 12 and the iris 16 and the exposed area of the lens 30; and the posterior chamber, between the iris 16 and the lens 30. The lens 30 is suspended to the ciliary body 22 by the suspensory ciliary ligament 32 (Zonule of Zinn), made up of fine transparent fibers. The vitreous body 26 is a clear jelly that is much larger than the aqueous humor.

The crystalline lens 30 is a transparent, biconvex structure in the eye that, along with the cornea 12, helps to refract light to be focused on the retina 24. The lens 30, by changing its shape, functions to change the focal distance of the eye so that it can focus on objects at various distances, thus allowing a sharp real image of the object of interest to be formed on the retina 24. This adjustment of the lens 30 is known as accommodation, and is similar to the focusing of a photographic camera via movement of its lenses.

The lens has three main parts: the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are found predominantly on the anterior side of the lens but extend posteriorly just beyond the equator.

The lens capsule is a smooth, transparent basement membrane that completely surrounds the lens. The capsule is elastic and is composed of collagen. It is synthesized by the lens epithelium and its main components are Type IV collagen and sulfated glycosaminoglycans (GAGs). The capsule is very elastic and so causes the lens to assume a more globular shape when not under the tension of the zonular fibers, which connect the lens capsule to the ciliary body 22. The capsule varies between approximately 2-28 micrometers in thickness, being thickest near the equator and thinnest near the posterior pole. The lens capsule may be involved with the higher anterior curvature than posterior of the lens.

Various diseases and disorders of the lens 30 may be treated with an IOL. By way of example, not necessarily limitation, a modular IOL according to embodiments of the present disclosure may be used to treat cataracts, large optical errors in myopic (near-sighted), hyperopic (far-sighted), and astigmatic eyes, ectopia lentis, aphakia, pseudophakia, and nuclear sclerosis. However, for purposes of description, the modular IOL embodiments of the present disclosure are described with reference to cataracts.

The following detailed description describes various embodiments of a modular IOL system including primary and secondary intraocular components, namely an intraocular base configured to releasably receive an intraocular lens. In some embodiments, the base may be configured to provide optical correction, in which case the modular IOL system may be described as including a primary lens and a secondary lens. The principles and features described with reference to embodiments where the base is configured for optical correction may be applied to embodiments where the base is not configured for optical correction, and vice versa. Stated more broadly, features described with reference to any one embodiment may be applied to and incorporated into other embodiments.

Figure 2A:
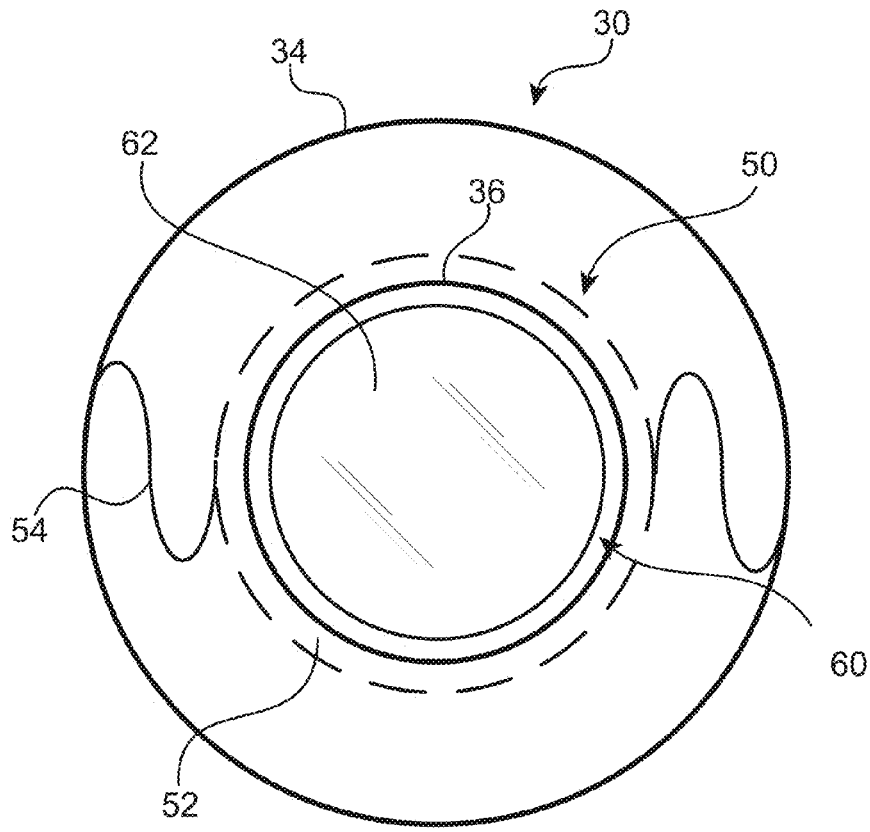
FIGS. 2A and 2B are front and side cross-sectional views, respectively, of a modular IOL disposed in a capsular bag according to an embodiment of the present disclosure.
Figure 2B:
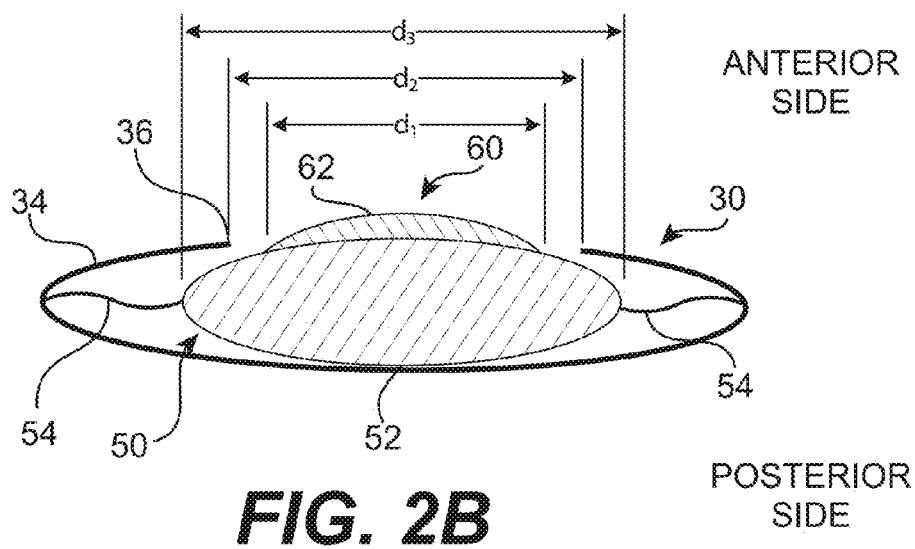

With reference to FIGS. 2A and 2B, a modular IOL system 50/60 is shown implanted in the capsular bag 34 of lens 30 having a capsulorhexis 36 formed therein. The modular IOL system may include a primary lens 50 and a secondary lens 60. The primary lens 50 may include a body portion 52, a pair of haptics 54 for anchoring and centering the primary lens 50 in the capsular bag 34, and means for attachment (not shown here, but described later) to the secondary lens 60. The secondary lens 60 may include an optic body portion 62, no haptics, and corresponding means for attachment (not shown here, but described later) to the primary lens 50. The anterior surface of the body portion 52 of the primary lens 50 may be in intimate contact with the posterior surface of the body portion 62 of the secondary lens 60, without any intervening material (e.g., adhesive, aqueous humor, tissue ingrowth, etc.) in between. For example, the anterior surface of the body portion 52 may be in directed contact with the posterior surface of body portion 62. The secondary lens 60 may be acutely and chronically releasably attached to the primary lens 50 to facilitate exchange of the secondary lens 60 while the primary lens 50 remains in the capsular bag 34 of the lens 30.

The body portion 52 of the primary lens 50 may provide some refractive correction, but less than required for an optimal optical result. The optimal optical result may be provided by the combination of the correction provided by the optical body portion 52 of the primary lens 50 together with the optical body portion 62 of the secondary lens 60. For example, the optical body portion 62 of the secondary lens 60 may change (e.g., add or subtract) refractive power (for monofocal correction), toric features (for astigmatism correction), and/or diffractive features (for multifocal correction).

The secondary lens 60 may have an outside diameter d1, the capsulorhexis 36 may have an inside diameter d2, and the body 52 of the primary lens 50 may have an outside diameter d3, where $d1 < d2 \leq d3$. This arrangement provides a gap between the secondary lens 60 and the perimeter of the capsulorhexis 36 such that the secondary lens 60 may be attached or detached from the primary lens 50 without touching or otherwise disturbing any portion of the capsular bag 34. By way of example, not limitation, assuming the capsulorhexis has a diameter of approximately 5 to 6 mm, the body of the primary lens (i.e., excluding the haptics) may have a diameter of approximately 5 to 8 mm, and the secondary lens may have a diameter of approximately 3 to less than 5 mm, thereby providing a radial gap up to approximately 1.5 mm between the secondary lens and the perimeter of the capsulorhexis. Notwithstanding this example, any suitable dimensions may be selected to provide a gap between the secondary lens and the perimeter of the capsulorhexis in order to mitigate the need to manipulate the lens capsule to attach the secondary lens to the primary lens.

Figure 3A:
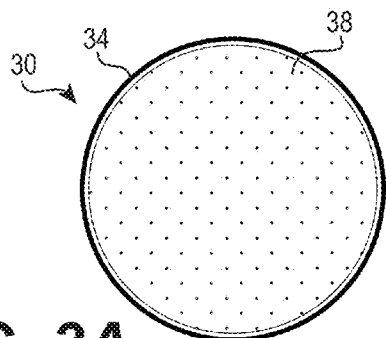
FIGS. 3A-3D and 4A-4D are front and side cross-sectional views, respectively, schematically illustrating a method for implanting a modular IOL according to an embodiment of the present disclosure.
Figure 4A:
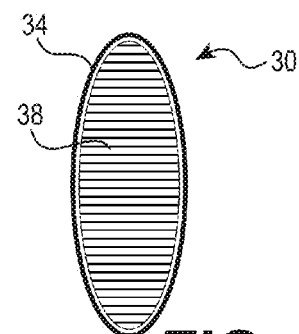
Figure 3B:
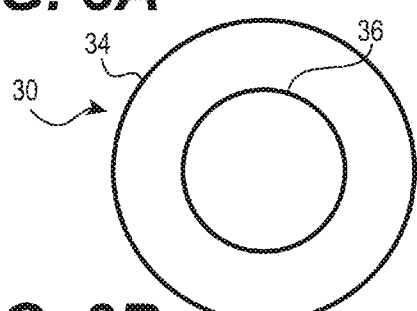
Figure 4B:
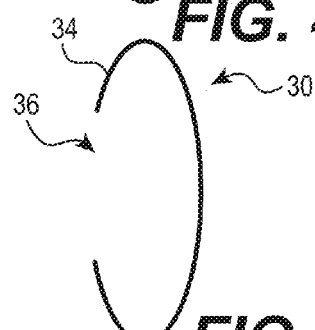
Figure 3C:
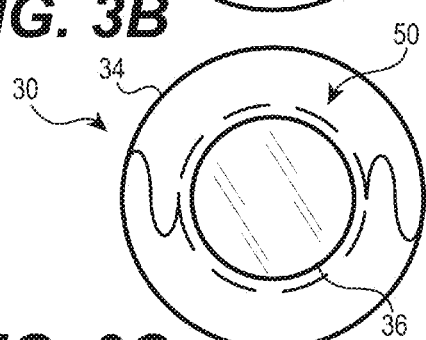
Figure 4C:
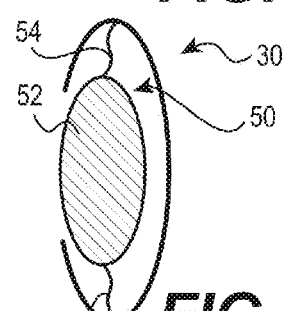
Figure 3D:
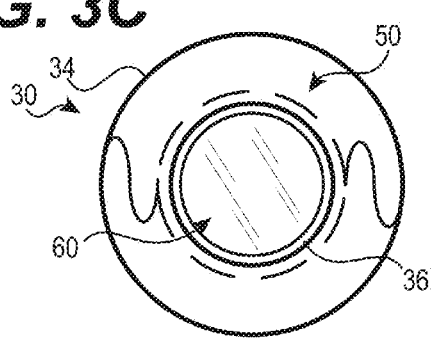
Figure 4D:
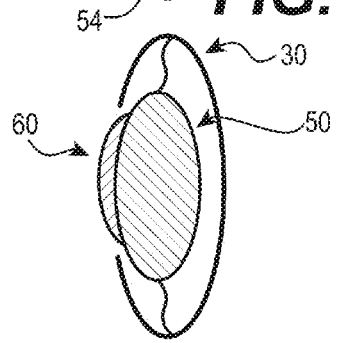

With reference to FIGS. 3A-3D (front views) and 4A-4D (side cross-sectional views), a method for implanting a modular IOL system 50/60 is shown schematically. As seen in FIGS. 3A and 4A, a lens 30 with cataracts includes an opaque or clouded center 38 inside a capsular bag 34. Access to the lens 30 for cataract surgery may be provided by one or more lateral incisions in the cornea. A capsulorhexis (circular hole) 36 may be formed in the anterior capsular bag 34 using manual tools or a femtosecond laser. As seen in FIGS. 3B and 4B, the opaque center 38 is removed by phacoemulsification and/or aspiration through the capsulorhexis 36. The primary lens 50 is delivered in a rolled configuration using a tube inserted through the capsulorhexis 36 and into the capsular bag 34. The primary lens 50 is ejected from the delivery tube and allowed to unfurl. With gentle manipulation, the haptics 54 of the primary lens engage the inside equator of the lens capsule 34 and center the lens body 52 relative to the capsulorhexis 36 as seen in FIGS. 3C and 4C. The secondary lens 60 is delivered in a rolled configuration using a tube, positioning the distal tip thereof adjacent the primary lens 50. The secondary lens 60 is ejected from the delivery tube and allowed to unfurl. With gentle manipulation, the secondary lens 60 is centered relative to the capsulorhexis 36. Without manipulating the capsular bag 34 or the primary lens 50, the secondary lens 60 is then attached to the primary lens 50 as seen in FIGS. 3D and 4D. If necessary, the secondary lens 60 may be removed and/or replaced in a similar manner, reversing the steps where appropriate. As an alternative, the primary 50 and secondary 60 lenses may be implanted as a unit, thus eliminating a delivery step.

Because it may be difficult to ascertain which side of the secondary lens 60 should face the primary lens 50, the secondary lens may include a marking indicative of proper position. For example, a clockwise arrow may be placed along the perimeter of the anterior surface of the secondary lens 60, which appears as a clockwise arrow if positioned right-side-up and a counter-clockwise arrow if positioned wrong-side-up. Alternatively, a two-layered color marking may be placed along the perimeter of the anterior surface of the secondary lens 60, which appears as a first color if positioned right-side-up and a second color if positioned wrong-side-down. Other positionally indicative markings may be employed on the secondary lens 60, and similar marking schemes may be applied to the primary lens 50.

Figure 5:
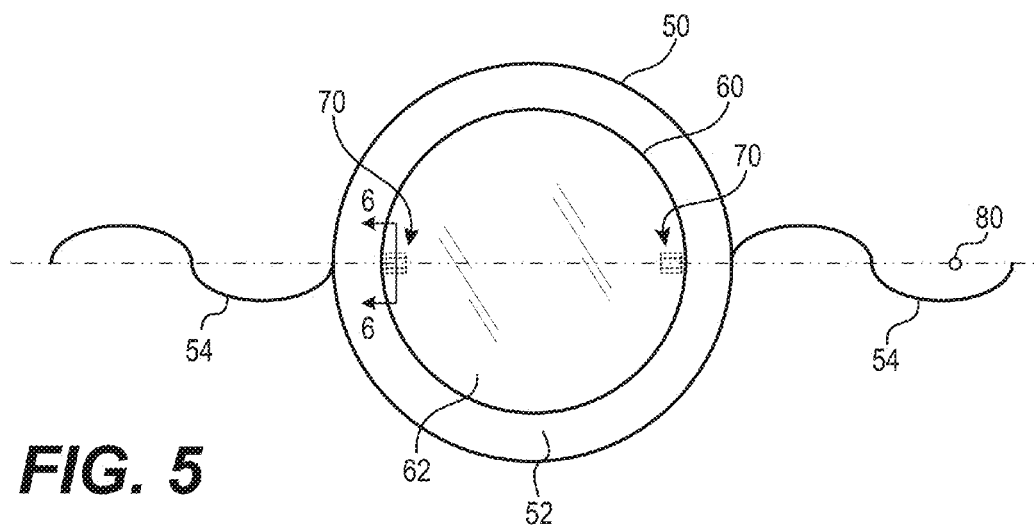
FIG. 5 is a front view of a modular IOL, according to an embodiment of the present disclosure, wherein subsurface attachment mechanisms are provided for connection between the primary and secondary lenses.

With reference to FIG. 5, subsurface attachment mechanisms 70 may be used to releasably secure the secondary lens 60 to the primary lens 50. The attachment mechanisms 70 may be positioned radially inside the perimeter of the capsulorhexis 36 and radially outside the field of view to avoid interference with light transmission. Alternatively or in addition, the attachment mechanism 70 may have radial and lateral extents limited to a small fraction (e.g., less than 10-20%) of the perimeter of the secondary lens 50 to minimize the potential for interference in light transmission. Two diametrically opposed attachment mechanisms 70 are shown, but any suitable number may be used, uniformly or non-uniformly distributed about the circumference of the secondary lens 60.

If the primary lens 50 and the secondary lens 60 are delivered at the same time, it may be desirable to align the attachment mechanisms 70 with the roll axis 80, around which the lenses 50 and 60 may be rolled for insertion via a delivery tool. Because the secondary lens 60 may shift relative to the primary lens 50 when rolled about axis 80, providing the attachment mechanisms 70 along the roll axis 80 minimizes stress to the attachment mechanisms 70. To this end, the attachment mechanisms 70 may be coaxially aligned relative to the roll axis 80 and may be configured to extend a limited distance (e.g., less than 10-20% of the perimeter of the secondary lens 60) from the axis 80.

Figure 6A:
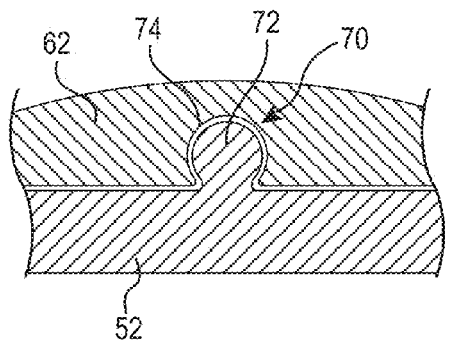
FIGS. 6A and 6B are cross-sectional views taken along line 6-6 in FIG. 5, showing two embodiments of subsurface attachment mechanisms.
Figure 6B:
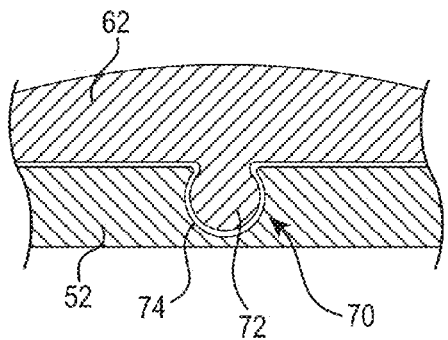

The attachment mechanisms 70 may be configured to have mating or interlocking geometries as shown in FIGS. 6A and 6B. Generally, the geometries include a male portion and female portion that are releasably connectable. The female portion is configured to receive the male portion and limit relative motion between the primary lens 50 and the secondary lens 60 in at least two dimensions (e.g., superior-inferior and right-left). The female and male portions may be configured to have an interlocking geometry such that relative motion between the primary lens 50 and the secondary lens 60 is limited in three dimensions (e.g., superior-inferior, right-left, anterior-posterior). The attachment mechanisms 70 may be engaged and disengaged by applying orthogonal force in a posterior (push) and anterior (pull) direction, respectively. The attachment mechanisms 70 may be pre-formed by molding, cutting, etching, or a combination thereof, for example.

In the examples shown, each attachment mechanism 70 comprises an interlocking cylindrical protrusion 72 and cylindrical recess or groove 74. Other mating or interlocking geometries may be used as well. The cylindrical geometry shown has the advantage of allowing slight rotation of the secondary lens 60 relative to the primary lens 50 when rolled for delivery, thus further reducing stress thereon. As shown in FIG. 6A, the cylindrical protrusion 72 may extend anteriorly from the anterior surface of the body 52 of the primary lens 50, and the cylindrical recess 74 may extend anteriorly through the posterior surface of the body 62 of the secondary lens 60 adjacent a radial peripheral zone thereof. Alternatively, as shown in FIG. 6B, the cylindrical protrusion 72 may extend posteriorly from the posterior surface of the body 62 of the secondary lens 60 adjacent a radial peripheral zone thereof, and the cylindrical recess 74 may extend posteriorly through the anterior surface of the body 52 of the primary lens 50. The configuration shown in FIG. 6B may be particularly suited for the case where the primary lens 50 is a pre-existing implanted IOL into which the recess 74 may be etched in-situ, by laser, for example.

Figure 7:
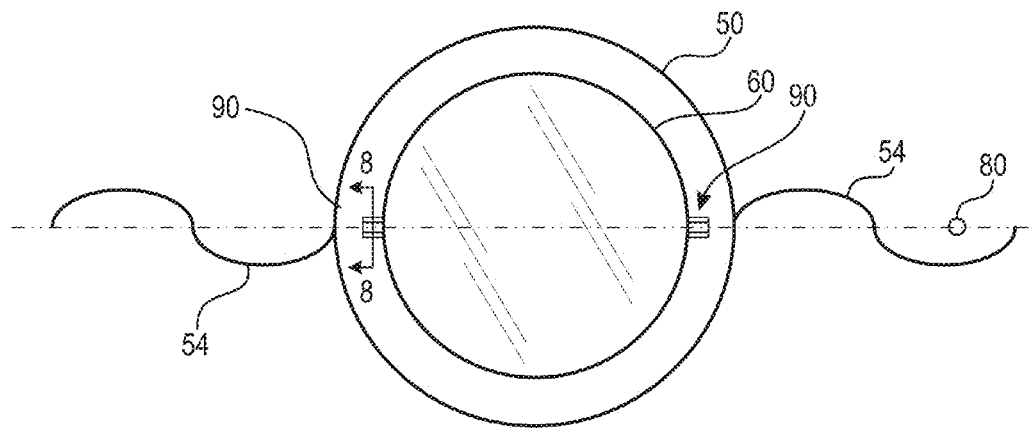
FIG. 7 is a front view of a modular IOL, according to an embodiment of the present disclosure, wherein extension attachment mechanisms are provided to connect the primary and secondary lenses.
Figure 8A:
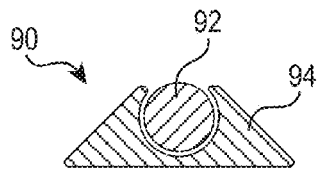
FIGS. 8A-8C are cross-sectional views taken along line 8-8 in FIG. 7, showing three embodiments of extension attachment mechanisms.
Figure 8B:
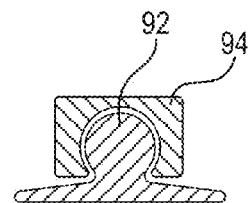
Figure 8C:
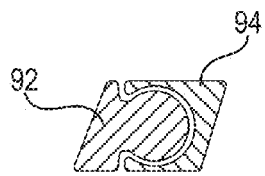

With reference to FIG. 7, extension attachment mechanisms 90 may be used to releasably connect the primary 50 and secondary 60 lenses. Extension attachment mechanisms 90 may be similar to subsurface attachment mechanisms 70 except as shown and described. Extension attachment mechanisms 90 may extend radially from the perimeter of the secondary lens 60, with each including mating or interlocking geometries, examples of which are shown in FIGS. 8A-8C. In FIG. 8A, a cylindrical portion 92 extends from the outer edge of the secondary lens 60, and a cylindrical recess 94 extends from the outer edge of the primary lens 50. In FIG. 8B, the corollary is shown, with the cylindrical portion 92 extending from the outer edge of the primary lens 50, and the cylindrical recess 94 extending from the outer edge of the secondary lens 60. In both embodiments shown in FIGS. 8A and 8B, the attachment mechanisms 90 may be engaged and disengaged by applying orthogonal force in a posterior (push) and anterior (pull) direction, respectively. Alternatively, in the embodiment shown in FIG. 8C, the attachment mechanisms 90 may be engaged and disengaged by applying rotational force in a clockwise or counterclockwise direction, depending on which lens 50/60 is attached to each of the cylindrical portion 92 and the cylindrical recess 94. In addition, although the embodiment of FIG. 7 only depicts the use of two attachment mechanisms 90, any suitable number of attachment mechanisms 90 may be utilized within the principles of the present disclosure.

Figure 9A:
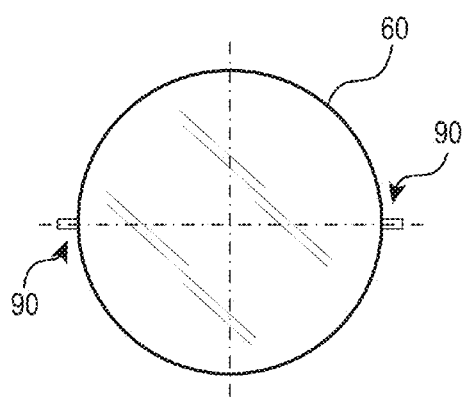
FIGS. 9A-9D are front views showing various positions of the attachment mechanisms to adjust the position of the secondary lens relative to the primary lens.
Figure 9B:
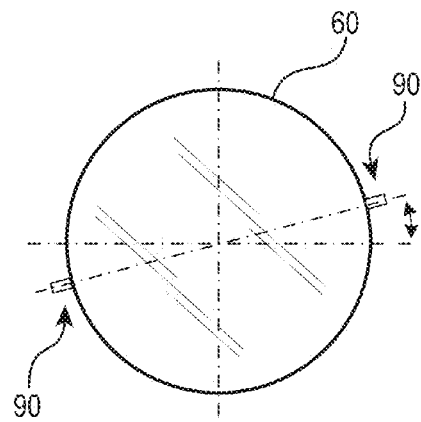
Figure 9C:
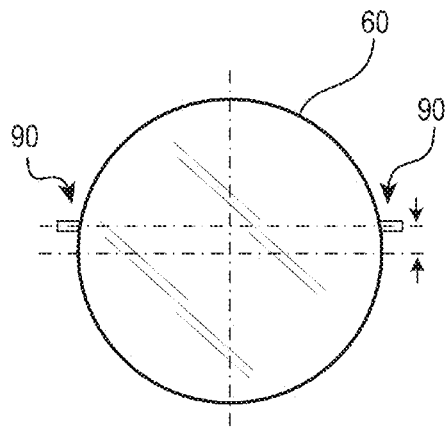
Figure 9D:
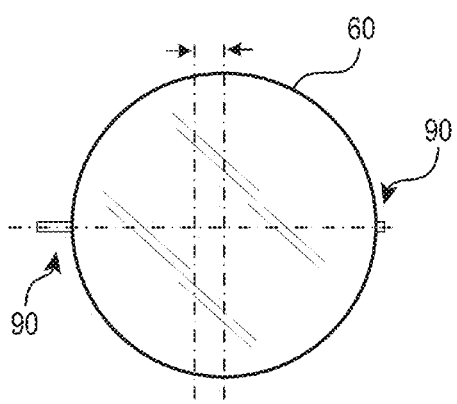

With reference to FIGS. 9A-9D, the portion of attachment mechanism 90 associated with the secondary lens 60 may be positioned such that the center of the secondary lens 60 is aligned with the center of the primary lens 50. Alternatively, to adjust for misalignment of the primary lens 50 due to imbalanced post-operative healing, for example, the portion of attachment mechanism 90 associated with the secondary lens 60 may be offset as shown in FIGS. 9B-9D. In FIG. 9B, the portion of attachment mechanism 90 associated with the secondary lens 60 is rotationally offset. In FIG. 9C, the portion of attachment mechanism 90 associated with the secondary lens 60 is superiorly offset. In FIG. 9D, the portion of attachment mechanism 90 associated with the secondary lens 60 is laterally offset. An anterior-posterior offset may also be employed as described in more detail with reference to FIGS. 11C and 11F. Each of the embodiments shown in FIGS. 9B, 9C, 9D, 11C and 11F are provided by way of example, and the offset may be made in any direction (anterior, posterior, superior, inferior, right, left, clockwise, counterclockwise) or combination thereof, to varying magnitudes depending on the misalignment of the primary lens 50. In addition, attachment mechanism 90 is shown by way of example, but the same principles may be applied to other attachment means described herein.

Figure 10:
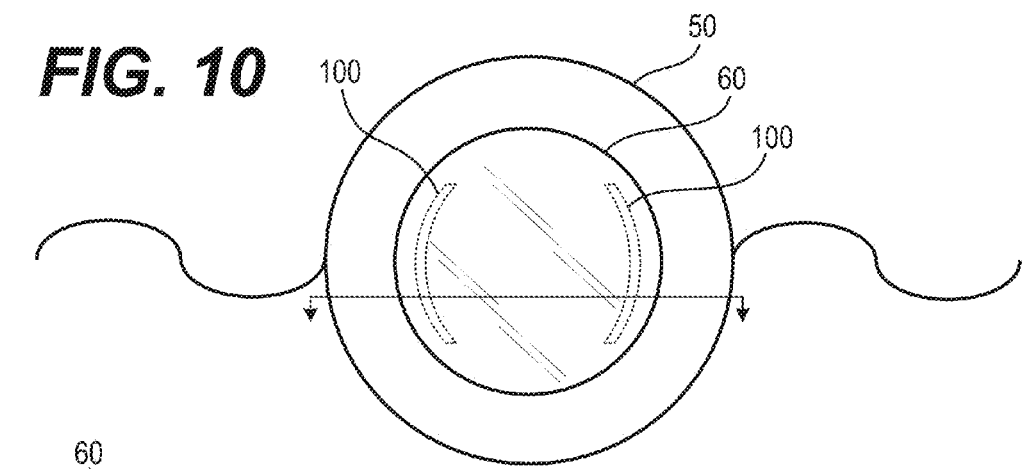
FIG. 10 is a front view of a modular IOL, according to an embodiment of the present disclosure, wherein etched subsurface attachment mechanisms are provided for connection between the primary and secondary lenses.
Figure 11A:
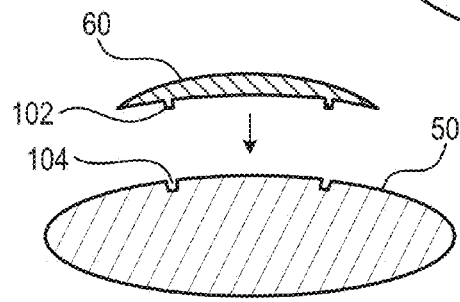
FIGS. 11A-11F are cross-sectional views of the modular IOL shown in FIG. 10, showing various embodiments of etched subsurface attachment mechanisms.
Figure 11B:
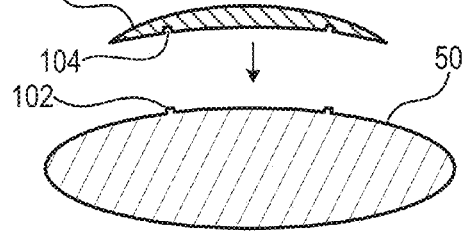
Figure 11C:
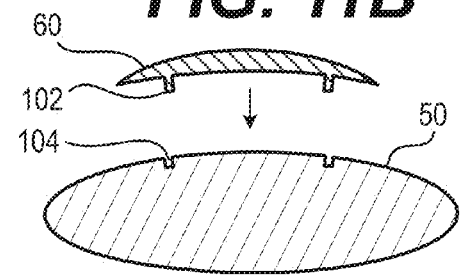
Figure 11D:
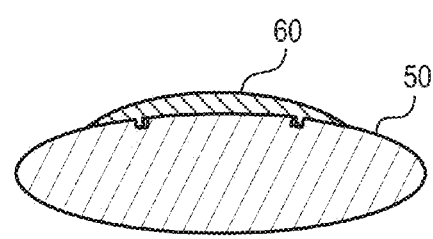
Figure 11E:
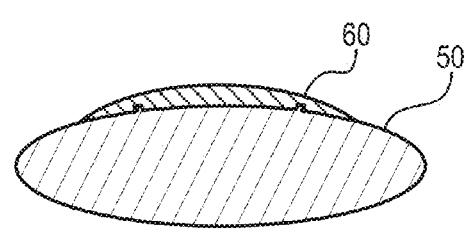
Figure 11F:
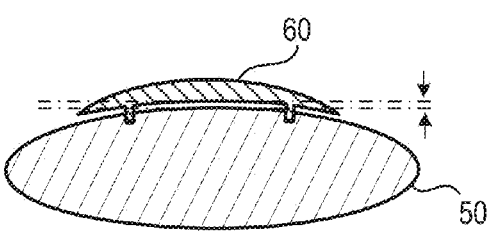

With reference to FIG. 10, alternative subsurface attachment mechanisms 100 may be used to releasably connect the secondary lens 50 to the primary lens 60. Subsurface attachment mechanisms 100 may be similar to subsurface attachment mechanisms 70 except as shown and described. Subsurface attachment mechanisms 100 may comprise mating or interlocking geometries extending along an arcuate path adjacent the peripheral edge of the secondary lens 60. The subsurface attachment mechanism 100 may include a protrusion 102 and a corresponding recess or groove 104 into which the protrusion 102 may be received. The protrusion 102 may extend from the posterior surface of the secondary lens 60 and the corresponding recess or groove 104 may extend into the anterior surface of the primary lens 50 as shown in FIGS. 11A (separated) and 11D (attached). Alternatively, the protrusion 102 may extend from the anterior surface of the primary lens 50 and the corresponding the recess or groove 104 may extend into the posterior surface of the secondary lens 60 as shown in FIGS. 11B (separated) and 11E (attached). In either embodiment, the anterior-posterior dimension of the protrusion 102 may match the same dimension of the recess or groove 104 to provide intimate contact between the anterior surface of the primary lens 50 and the posterior surface of the secondary lens 60. Alternatively, the anterior-posterior dimension of the protrusion 102 may exceed the same dimension of the recess or groove 104 to provide an anterior-posterior offset as shown in FIGS. 11C (separated) and 11F (attached). Further, those of ordinary skill in the art will readily recognize that any suitable number of attachment mechanisms 100 may be utilized within the principles of the present disclosure.

Figure 12A:
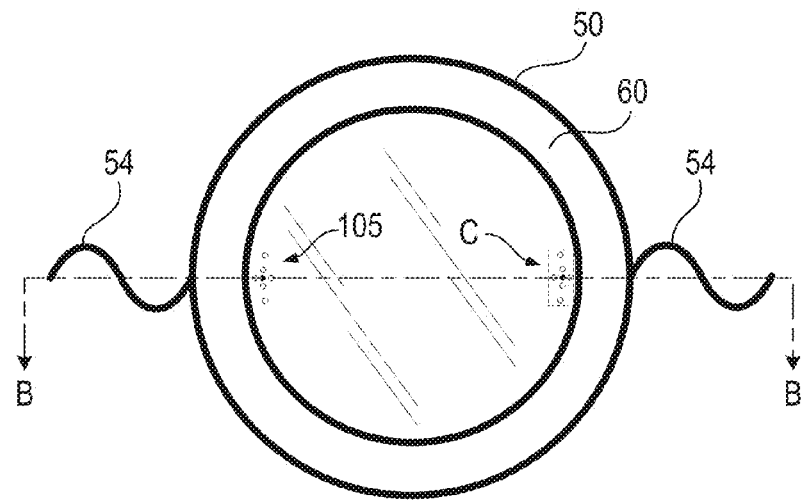
FIGS. 12A-12C are schematic illustrations of front, sectional and detail views, respectively, of an alternative modular IOL, according to an embodiment of the present disclosure.
Figure 12B:
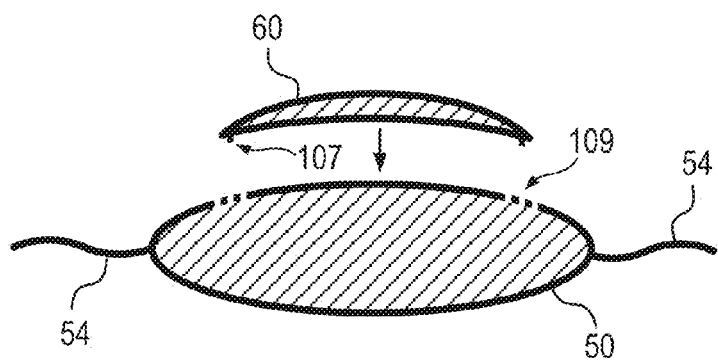
Figure 12C:
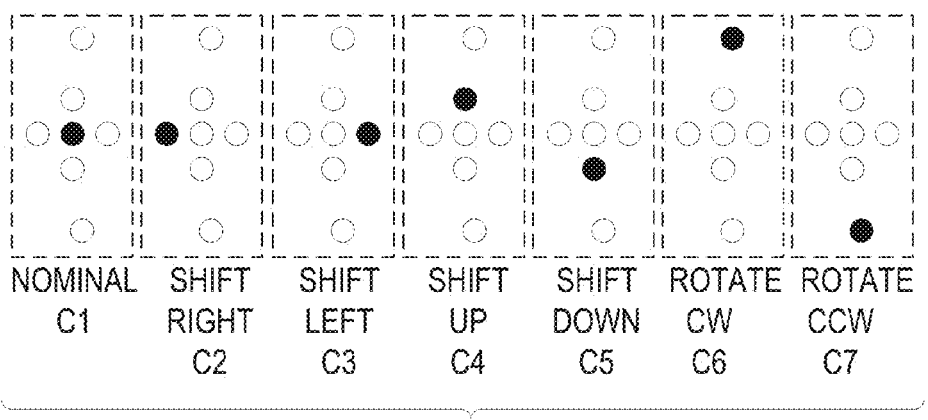

With reference to FIG. 12A, alternative subsurface attachment mechanisms 105 may be used to connect the secondary lens 60 to the primary lens 50. Subsurface attachment mechanisms 105 may be similar to subsurface attachment mechanisms 100 except as shown and described. As seen in FIG. 12B, which is a cross-sectional view taken along line B-B in FIG. 12A, the subsurface attachment mechanism 105 may comprise mating or interlocking geometries including a protrusion 107 and a series of holes 109 into which the protrusion 107 may be received. The holes 109 may be distributed in a pattern as seen in FIG. 12C, which shows several alternative detail views of box C in FIG. 12A. In FIG. 12C, the protrusion 107 resides in a hole 109 designated as a black circle while the remaining holes 109 designated as white circles remain open. With this arrangement, the protrusions 107 may be placed in a corresponding pair of holes 109 to achieve the desired alignment between the primary 50 and secondary 60 lenses. For example, and with continued reference to FIG. 12C, the protrusions 107 may be placed in a corresponding pair of holes 109 to achieve centered (nominal), shift right, shift left, shift up, shift down, rotate clockwise or rotate counterclockwise (labeled C1-C7, respectively) alignment between the primary 50 and secondary 60 lenses. This arrangement provides a range of adjustments as described with reference to FIGS. 9A-9D. In addition, any suitable number of attachment mechanisms 105 may be disposed uniformly or non-uniformly about a perimeter of lenses 50 and 60.

All or a portion of the various subsurface attachment means described herein may be formed by molding, cutting, milling, etching or a combination thereof. For example, with particular reference to FIG. 11A, the groove 104 may be formed by in-situ laser etching a pre-existing implanted primary lens 50, and the protrusion may be pre-formed by molding, milling or cutting the secondary lens 60.

Examples of lasers that may be used for in-situ etching include femtosecond lasers, ti/saph lasers, diode lasers, YAG lasers, argon lasers and other lasers in the visible, infrared and ultraviolet range. Such lasers may be controlled in terms of energy output, spatial control and temporal control to achieve the desired etch geometry and pattern. In-situ etching may be accomplished, for example, by transmitting a laser beam from an external laser source, through the cornea and past the pupil. Alternatively, in-situ etching may be accomplished by transmitting a laser beam from a flexible fiber optic probe inserted into the eye.

Figure 13A:
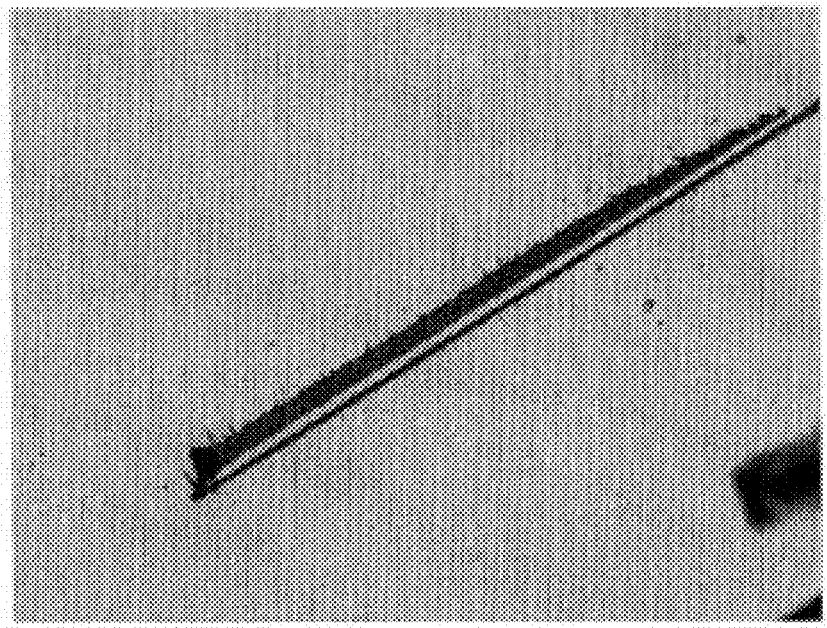
FIGS. 13A and 13B show representative photomicrographs at 4× and 40× magnification, respectively, of a groove (see, arrow) formed by laser etching.
Figure 13B:
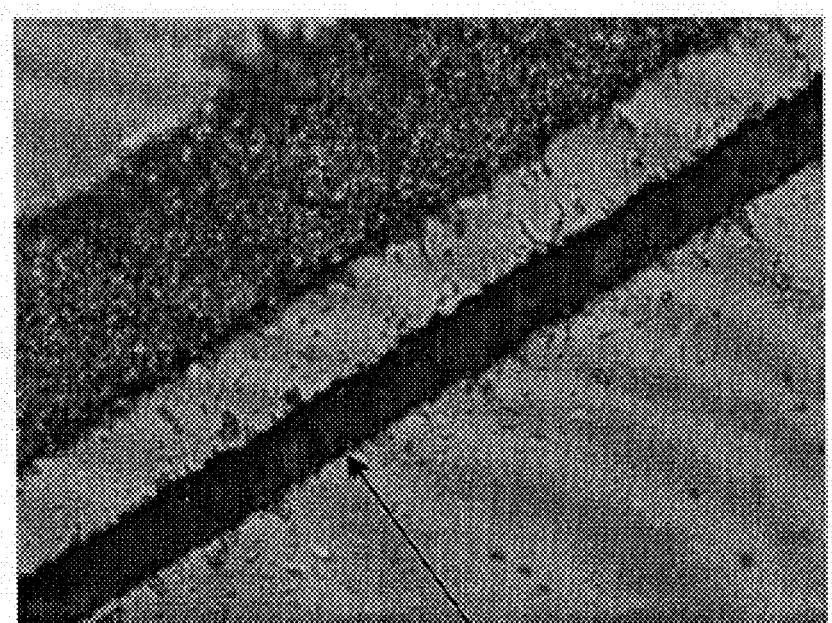

With reference to FIGS. 13A and 13B, photomicrographs at 4× and 40× magnification, respectively, show how a groove (see, arrow) was experimentally etched in a primary lens by laser etching. A femtosecond laser set within the following ranges may be used to etch the groove: power of 1 nJ to 100 uJ; pulse duration of 20 fs up to the picosecond range; and a frequency of 1 to 250 kHz.

The primary and secondary components of the modular IOL systems disclosed herein may be formed of the same, similar or dissimilar materials. Suitable materials may include, for example, acrylate-based materials, silicone materials, hydrophobic polymers or hydrophilic polymers, and such materials may have shape-memory characteristics. For example, materials comprising the optical portions of the modular lens system can be silicone, PMMA, hydrogels, hydrophobic acrylic, hydrophilic acrylic or other transparent materials commonly used for intraocular lenses. Non-optical components of the modular IOL might include nitinol, polyethylene sulfone and/or polyimide.

Materials can be selected to aid performance of certain features of the modular lens system notably the attachment and detachment features necessary for the primary and secondary lenses as previously described. Other features of the modular lens that can be enhanced with specific material selections include manufacturability, intraoperative and post-operative handling, fixation (both intraoperative and at time of post-operative modification), reaching micro-incision sizes (≤2.4 mm) and exchangeability (minimal trauma on explantation of lenses).

For example, in one embodiment the primary lens and the secondary lens are made from hydrophobic acrylic material having a glass transition temperature between approximately 5 and 30° C. and a refractive index between approximately 1.41-1.60. In another embodiment, the primary and secondary lens can be made from different materials having different glass transition temperatures and mechanical properties to aid fixation and detachment properties of the modular system. In another embodiment, both or either of the modular lens system is made from materials allowing for compression to an outer diameter equal to or smaller than approximately 2.4 mm.

Material properties that are generally desirable in the modular IOL system include minimal to no glistening formation, minimal pitting when exposed to YAG laser application and passing standard MEM elution testing and other biocompatibility testing as per industry standards. The material may contain various chromophores that will enhance UV blocking capabilities of the base material. Generally, wavelengths that are sub 400 nm are blocked with standard chromophores at concentrations ≤1%. Alternatively or in addition, the material may contain blue light blocking chromophores, e.g., yellow dyes which block the desired region of the blue-light spectrum. Suitable materials are generally resistant to damage, e.g., surface abrasion, cracking, or hazing, incurred by mechanical trauma under standard implantation techniques.

The components of the modular IOL may be formed by conventional techniques such as molding, cutting, milling, etching or a combination thereof.

As an alternative to mechanical attachment, chemical attraction between the primary and secondary components may be utilized. Using similar materials with a smooth surface finish may facilitate chemical attraction. Chemical attraction may be enhanced by surface activation techniques such as plasma or chemical activation. In some instances, it may be desirable to reduce chemical attraction to avoid sticking between the materials and rely more on mechanical attachment for stability. In this case, the primary and secondary components may be formed of dissimilar materials or otherwise have adjacent surfaces that do not have a chemical attraction.

With reference to FIGS. 14-14C, an alternative modular IOL 140 is shown in front, sectional and detailed views, respectively. FIG. 14A shows a cross-sectional view taken along line A-A in FIG. 14, FIG. 14B shows a cross sectional view taken along line B-B in FIG. 14, and FIG. 14C shows a detail view of circle C in FIG. 14B. Modular IOL 140 may include a primary lens 50 with haptics 54 and a secondary lens 60. The interfacing surfaces of the primary lens 50 (anterior surface) and secondary lens 60 (posterior surface) may be in intimate contact as best seen in FIGS. 14A and 14B. Maintaining intimate contact (i.e., avoiding a gap) or maintaining a consistent gap between the interfacing surfaces of the primary lens 50 and the secondary lens 60 may reduce the likelihood of induced astigmatism. In some embodiments, however, a substance (e.g., an adhesive agent) may be disposed between the respective surfaces of lenses 50 and 60. A circular extension may be formed in the secondary lens 60, with a correspondingly sized and shaped circular recess formed in the primary lens 50 to form an interference fit therebetween, thus securely connecting the two components. The depth of the recess in the primary lens 50 may be a fraction of the thickness of the secondary lens 60, with a circular extension of the secondary lens 60 extending over a portion of the primary lens 50, thereby forming an overlap joint 142 as best seen in FIG. 14C. The overlap joint 142 may extend 360 degrees around the circumference of the secondary lens 60 as shown, or a fraction thereof. The circular extension of the secondary lens 60 rises above the anterior surface of the primary lens 50 to form a raised portion. In some embodiments, the raised portion may have a radially tapering configuration. The raised portion may be radially compressed with forceps to facilitate connection and disconnection of the primary lens 50 and the secondary lens 60. Using radial compression to insert the secondary lens 60 into the primary lens 50 reduces the anterior-posterior forces applied to the capsular bag during insertion, thereby reducing the risk of capsular rupture.

With reference to FIGS. 15-15D, an alternative modular IOL 150 is shown in front, sectional and detailed views, respectively. FIG. 15A shows a cross-sectional view taken along line A-A in FIG. 15, FIG. 15B shows a cross sectional view taken along line B-B in FIG. 15, FIG. 15C shows a detail view of circle C in FIG. 15B, and FIG. 15D shows an alternative detail view of circle C in FIG. 15B. Modular IOL 150 may include a primary lens 50 with haptics 54 and a secondary lens 60. The interfacing surfaces of the primary lens 50 (anterior surface) and secondary lens 60 (posterior surface) may be in intimate contact as best seen in FIGS. 15A and 15B. The primary lens 50 may include a recess defining a wall into which the correspondingly sized and shaped circular secondary lens 60 may be placed. The wall defined by the recess in the primary lens 50 may extend around the entire perimeter of the primary lens with the exception of two diametrically opposed gaps 152. The gaps 152 thus expose the perimeter edge of the secondary lens 60 as seen in FIG. 15A to facilitate insertion and removal by radial compression of the secondary lens 60 using forceps, for example. The remainder of the wall defined by the recess in the primary lens provides for a flush joint as seen in FIGS. 15B and 15C, where the anterior surface of the secondary lens 60 may be flush with the anterior surface of the primary lens 50. As seen in FIG. 15C, the wall defined by the recess in the primary lens 50 and the interfacing edge of the secondary lens 60 may be canted inwardly to provide a joint 154 with positive mechanical capture and secure connection therebetween. Alternatively, as seen in FIG. 15D, the wall defined by the recess in the primary lens 50 and the interfacing edge of the secondary lens 60 may be "S" shaped to provide a joint 156 with positive mechanical capture and secure connection therebetween. Alternative interlocking geometries may be employed.

With reference to FIGS. 16-16D, an alternative modular IOL 160 is shown in front, sectional and detailed views, respectively. FIG. 16A shows a cross-sectional view taken along line A-A in FIG. 16, FIG. 16B shows a cross sectional view taken along line B-B in FIG. 16, FIG. 16C shows a detail view of circle C in FIG. 16B, and FIG. 16D shows a detail view of circle D in FIG. 16A. Modular IOL 160 may be configured similar to modular IOL 150 shown in FIGS. 15-15D with primary lens 50 including a recess defining a wall into which the correspondingly sized and shaped circular secondary lens 60 may be placed. However, in this embodiment, an angular gap 162 (rather than gap 152) is provided along a fraction of the perimeter of the secondary lens 60. The wall defined by a circumferential portion of the perimeter edge of the secondary lens 60 may have the same geometry as the wall defined by the recess in the primary lens 50 to provide a flush joint 154 as best seen in FIG. 16C. The wall defined by another (e.g., the remainder) circumferential portion of the perimeter edge of the secondary lens 60 may have a more inwardly angled geometry to provide an angled gap 162 as best seen in FIG. 16D. The angled gap 162 thus exposes the perimeter edge of the secondary lens 60 as seen in FIG. 16D into which forceps may be placed to facilitate insertion and removal by radial compression of the secondary lens 60. Alternative gap geometries may be employed.

Figure 17:
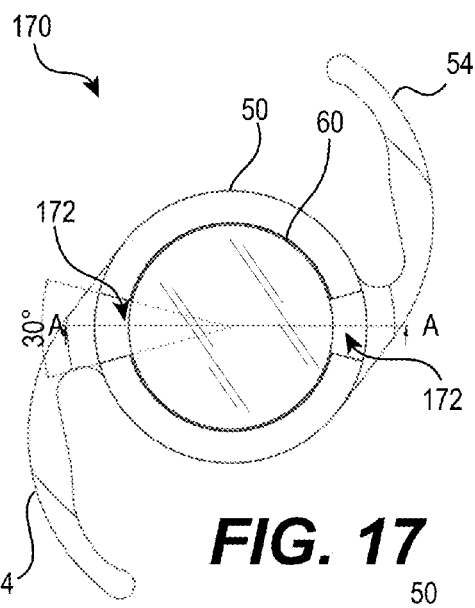
Figure 17B:
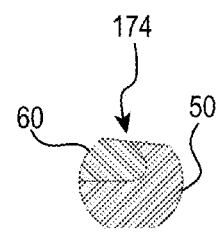
Figure 17A:
Figure 17C:
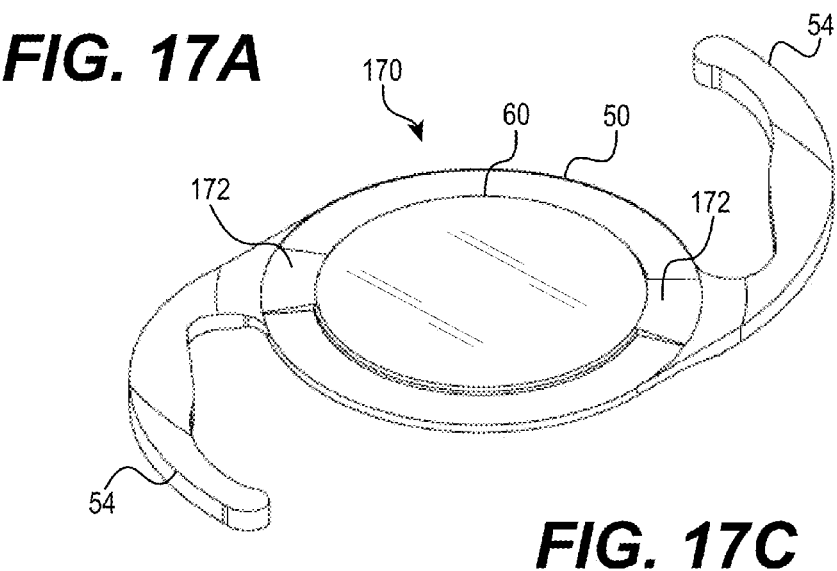

With reference to FIGS. 17-17C, an alternative modular IOL 170 is shown in front, sectional, detailed and isometric views, respectively. FIG. 17A shows a cross-sectional view taken along line A-A in FIG. 17, FIG. 17B shows a detail view of circle B in FIG. 17A, and FIG. 17C shows an isometric view of the assembled components. Modular IOL 170 may be configured similar to modular IOL 150 shown in FIGS. 15-15D with primary lens 50 including a recess defining a wall into which the correspondingly sized and shaped circular secondary lens 60 may be placed. However, in this embodiment, the wall defining the recess in the primary lens 50 includes a portion thereof that is milled down to define two diametrically opposed tabs 172. The inside circumferential walls of the tabs 172 provide for a flush joint 174 as seen in FIG. 17B, such that the anterior surface of the secondary lens 60 is flush with the anterior surface of the primary lens 50. The interface of the joint 174 along the tabs 172 may be canted, "S" shaped, or "C" shaped as shown, for example. Elsewhere along the perimeter, away from the tabs 172, in the area where the wall is milled down, the perimeter edge of the secondary lens 60 is exposed as seen in FIG. 17C, to facilitate insertion and removal of the secondary lens 60 by radial compression thereof using forceps, for example.

With reference to FIGS. 18-18C, an alternative modular IOL 180 is shown in front, sectional, detailed and isometric views, respectively. FIG. 18A shows a cross-sectional view taken along line A-A in FIG. 18, FIG. 18B shows a detail view of circle B in FIG. 18A, and FIG. 18C shows an isometric view of the assembled components. Modular IOL 180 may be configured similar to modular IOL 170 shown in FIGS. 17-17C with primary lens 50 including a recess defining a partial wall into which the correspondingly sized and shaped circular secondary lens 60 may be placed, interlocking via flush joint 174 in tabs 172. However, in this embodiment, grasping recesses or holes 182 are provided in each of the tabs 172 and in the adjacent portions of secondary lens 60. In one embodiment, the grasping recesses or holes 182 may not extend through an entire thickness of primary 50 and secondary 60 lenses. The grasping holes 182 in the secondary lens 60 facilitate insertion and removal by radial compression of the secondary lens 60 using forceps, for example. Adjacent grasping holes 182 in the tab portion 172 and the secondary lens 60 may be pulled together or pushed apart in a radial direction to facilitate connection and disconnection, respectively, of the joint 174 using forceps, for example.

Using radial forces applied via the grasping holes 182 to connect and disconnect (or lock and unlock) the joint 174 between the primary lens 50 and the secondary lens 60 reduces the anterior-posterior forces applied to the capsular bag, thereby reducing the risk of capsular rupture. Grasping holes 182 may also be used to facilitate connecting and disconnecting different interlocking geometries while minimizing anterior-posterior forces. For example, a recess in the primary lens 50 may include internal threads that engage corresponding external threads on the perimeter edge of the secondary lens 60. In this embodiment, forceps inserted into the grasping holes 182 may be used to facilitate rotation of the secondary lens 60 relative to the primary lens 50 to screw and unscrew the primary 50 and secondary 60 lenses. In an alternative embodiment, a keyed extension of the secondary lens 60 may be inserted into an keyed opening in the primary lens 50 and rotated using forceps inserted into the grasping holes 182 to lock and unlock the primary 50 and secondary 60 lenses. In another alternative embodiment, forceps or the like may be inserted posteriorly through a hole in the secondary lens 60 to grasp an anterior protrusion on the primary lens 50 like a handle (not shown), followed by applying posterior pressure to the secondary lens 60 while holding the primary lens 50 stationary. The grasping holes 182 may also be used to rotate the secondary lens 60 relative to the primary lens 50 for purposes of rotational adjustment in toric applications, for example.

With reference to FIGS. 19-19D, an alternative modular IOL 190 is shown in front, sectional, detailed and isometric exploded and isometric assembled views, respectively. FIG. 19A shows a cross-sectional view taken along line A-A in FIG. 19, FIG. 19B shows a detail view of circle B in FIG. 19A, FIG. 19C shows an exploded isometric view of the components, and FIG. 19D shows an assembled isometric view of the components. Modular IOL 190 differs from some of the previously described embodiments in that the primary component serves as a base 55 but does not necessarily provide for optical correction, whereas the secondary component serves as a lens 65 and provides for optical correction. Base 55 may be configured in the shape of an annulus or ring with a center opening 57 extending therethrough in an anterior-posterior direction. In some embodiments, base 55 may not define a complete ring or annulus. Base 55 may also include haptics 59, which are similar in function to haptics 54 described previously but differ in geometric configuration. Generally, haptics 54/59 function to center the base 55 in the capsular bag. Such haptics may also be configured to apply outward tension against the inside equatorial surface of the capsular bag, similar to capsular tension rings, to aid in symmetric healing and maintain centration of the base. The haptics 59 may include one or more openings therein.

Because the base 55 includes a center opening 57, the posterior optical surface of the lens 65 is not in contact with the base 55. A circular extension may be formed in the lens 65, with a correspondingly sized and shaped circular recess formed in the base 55 to form a ledge on the base 55 and an overlapping joint 192 with an interference and/or friction fit therebetween, thus securely connecting the two components. Alternatively, the shape of the overlapping joint 192 may form a canted angle or an "S" shape as described previously to form an interlock therebetween. The joint or junction 192 may include a modified surface to reduce light scattering caused by the junction 192. For example, one or both of the interfacing surfaces of the joint 192 may be partially to totally opaque or frosted (i.e., roughened surface) to reduce light scattering caused by the junction 192.

The depth of the recess in the base 55 may be the same thickness of the circular extension of the lens 65 such that the anterior surface of the lens 65 and the anterior surface of the base 55 are flush as best seen in FIG. 19B. With this arrangement, the posterior surface of the lens 65 extends more posteriorly than the anterior surface of the base 55. In some embodiments, however, the anterior surface of lens 65 may be disposed relatively higher or lower than the anterior surface of base 55. The dimensions of the recess and the corresponding ledge in the base 55 may be selected relative to the thickness of the lens 65 such that at least a portion of the posterior-most surface of the lens 65 is coplanar with the posterior-most surface of the base 55, or such that at least a portion of the posterior-most surface of the lens 65 is more posterior than the posterior-most surface of the base 55.

As with prior embodiments, the lens may be exchanged for a different lens either intra-operatively or post-operatively. This may be desirable, for example, if the first lens does not provide for the desired refractive correction, in which case the first lens may be exchanged for a second lens with a different refractive correction, without disturbing the lens capsule. In cases where the lens 65 does not have the desired optical alignment due to movement or misalignment of the base, for example, it may be exchanged for a different lens with an optical portion that is manufactured such that it is offset relative to the base 55. For example, the optical portion of the second lens may be offset in a rotational, lateral and/or axial direction, similar to the embodiments described with reference to FIGS. 9A-9D. This general concept may be applied to other embodiments herein where the secondary component (e.g., lens) has limited positional adjustability relative to the primary component (e.g., base).

A number of advantages are associated with the general configuration of this embodiment, some of which are mentioned hereinafter. For example, because the posterior optical surface of the lens 65 is not in contact with the base 55, the potential for debris entrapment therebetween is eliminated. Also, by way of example, because the base 55 includes a center opening 57 that is devoid of material, the base 55 may be rolled into a smaller diameter than a primary lens 50 as described previously to facilitate delivery through a smaller incision in the cornea. Alternatively, the base 55 may have a larger outside diameter and be rolled into a similar diameter as primary lens 50. For example, the base lens 55 may have an outside diameter (excluding haptics) of approximately 8 mm and be rolled into the same diameter as a primary lens 50 with an outside diameter 6 mm. This may allow at least a portion of the junction between the base 55 and lens 65 to be moved radially outward away from the circumferential perimeter of the capsulorhexis, which typically has a diameter of 5-6 mm. Moving at least a portion of the junction between the base 55 and the lens 65 radially outward from the perimeter of the capsulorhexis may reduce the amount of the junction that is in the field of view and thus reduce the potential for light scattering or optical aberrations (e.g., dysphotopsias) created thereby. Of course, notwithstanding this example, any suitable dimensions may be selected to provide a gap between the lens 65 and the perimeter edge of the capsulorhexis in order to mitigate the need to manipulate the lens capsule to connect or disconnect the lens 65 to or from the base 55.

Figure 20:
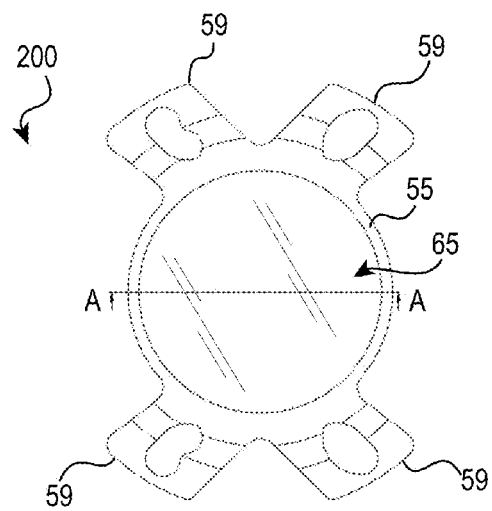
Figure 20A:
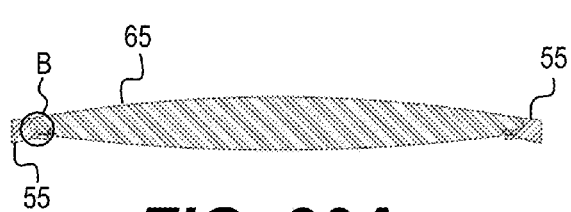
Figure 20B:
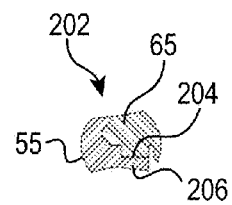
Figure 20C:
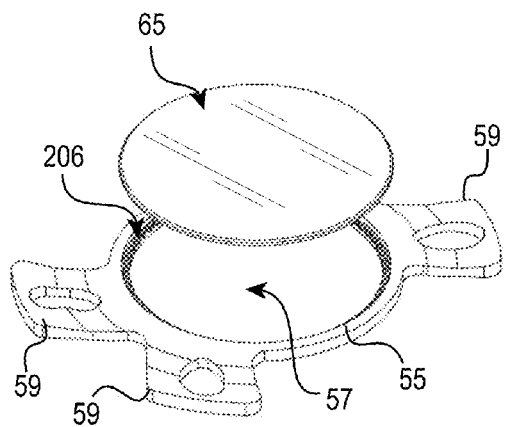
Figure 20D:
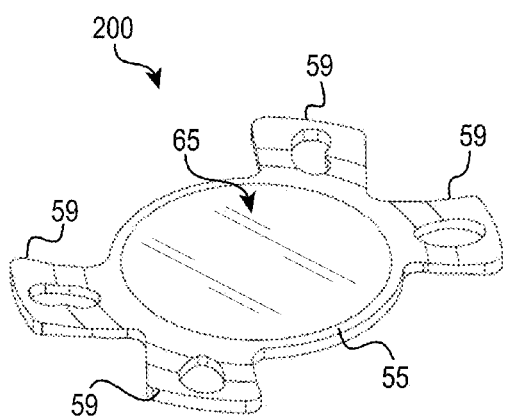

With reference to FIGS. 20-20D, an alternative modular IOL 200 is shown in front, sectional, detailed, isometric exploded and isometric assembled views, respectively. FIG. 20A shows a cross-sectional view taken along line A-A in FIG. 20, FIG. 20B shows a detail view of circle B in FIG. 20A, FIG. 20C shows an exploded isometric view of the components, and FIG. 20D shows an assembled isometric view of the components. Modular IOL 200 includes a base 55 with associated haptics 59 and a lens 65. The base 55 includes a center hole 57 such that the posterior optical surface of the lens 65 is not in contact with the base 55. The lens 65 includes a circular extension that is sized and shaped to fit in a circular recess formed in the base 55 to form a ledge on the base 55 and an overlapping joint 202. The overlapping joint 202 may be configured with an "S" shaped interface to securely connect the two components. Thus, modular IOL 200 is similar to modular IOL 190, except that the joint 202 between the base 55 and the lens 65 may include a peg-and-hole arrangement. In this arrangement, a pair of diametrically opposed pegs 204 may extend posteriorly from the posterior perimeter of the lens 65 and fit within a selected pair of holes 206 from a series of holes 206 formed in the ledge of the joint 202 in the base 55.

Figure 20E:
Figure 20F:
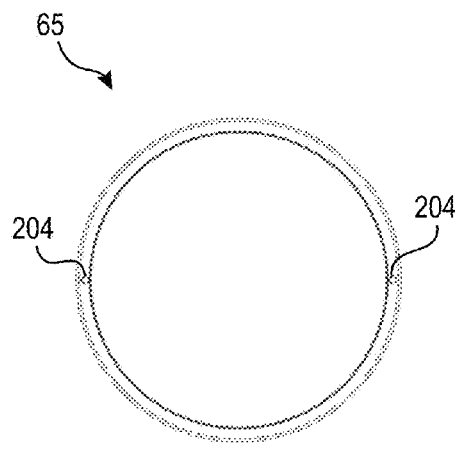
Figure 20G:
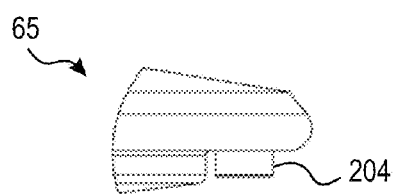
Figure 20H:
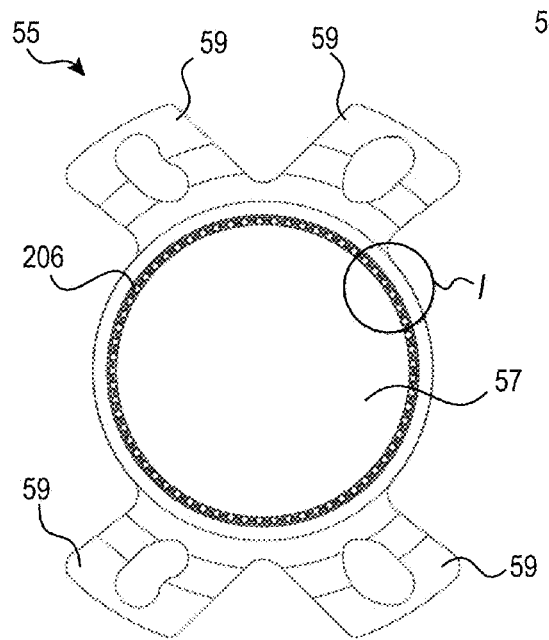
Figure 20I:
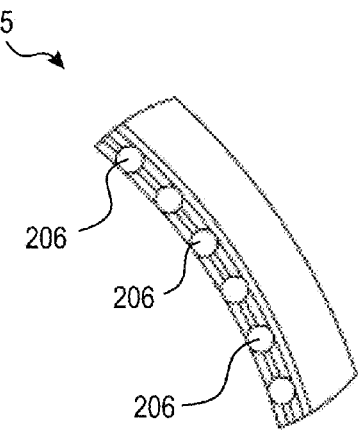

FIGS. 20E-20I show additional detail of modular IOL 200. FIG. 20E shows a side view of the lens 65, FIG. 20F shows a rear view of the posterior surface of the lens 65, FIG. 20G is a detailed view of circle G in FIG. 20E, FIG. 20H is a front view of the anterior surface of the base 55, and FIG. 20I is a detailed view of circle I in FIG. 20H. As seen in FIGS. 20E-20F, a pair of diametrically opposed pegs 204 may extend posteriorly from the posterior perimeter of the lens 65. As seen in FIGS. 20H-20I, the inside diameter of the base 55 along the ledge of the joint 202 includes a series of holes 206, into a selected pair of which the pair of pegs 204 may be inserted. With this arrangement, the lens 65 may be selectively rotated relative to the base 55 for purposes of rotational adjustment in toric applications, for example.

Figure 21:
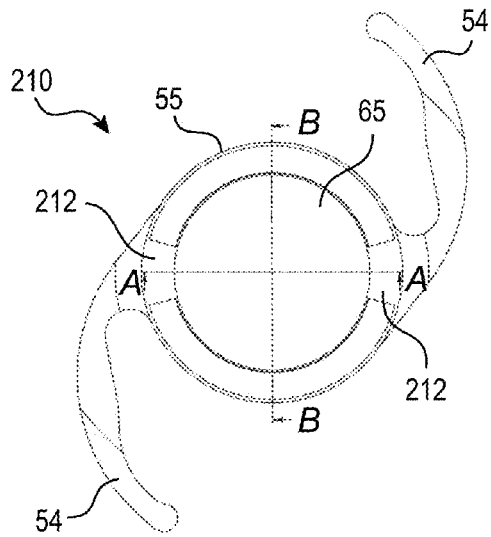
Figure 21B:
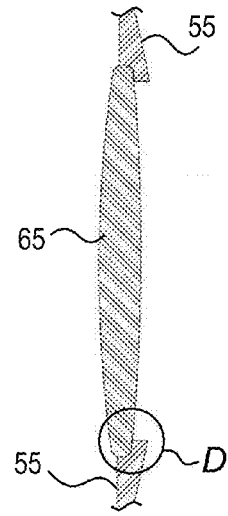
Figure 21A:
Figure 21C:
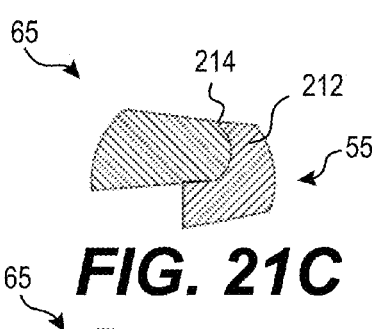
Figure 21D:
Figure 21E:
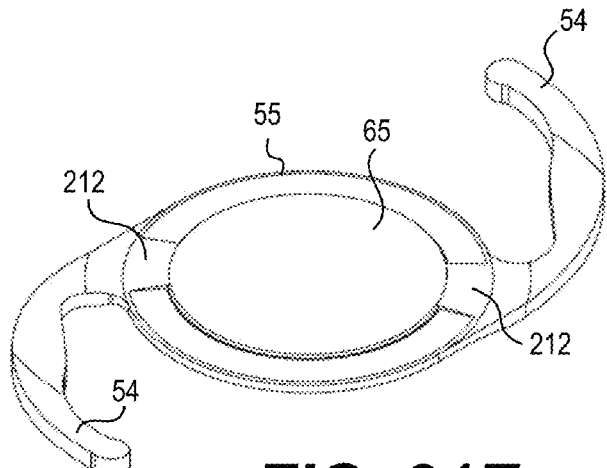

With reference to FIGS. 21-21E, an alternative modular IOL 210 is shown in front, sectional, detailed and isometric views, respectively. FIGS. 21A and 21B show a cross-sectional views taken along line A-A and line B-B, respectively, in FIG. 21. FIGS. 21C and 21D show detail views of circle C in FIG. 21A and circle D in FIG. 21B, respectively. FIG. 21E shows an isometric view of the assembled components of the modular IOL 210. Modular IOL 210 may be configured similar to a combination of modular IOL 190 shown in FIGS. 19-19D and modular IOL 170 shown in FIGS. 17-17C. Like modular IOL 190, modular IOL 210 includes a base 55 configured in the shape of an annulus or ring with a center opening and a recess defining a wall into which the correspondingly sized and shaped circular lens 65 may be placed. Like modular IOL 170, the wall defining the recess extends along the inside perimeter of the base 55, with a portion thereof milled down to define two diametrically opposed tabs 212. The inside circumferential walls of the tabs 212 provide for a flush joint 214 as seen in FIG. 21C, such that the anterior surface of the lens 65 is flush with the anterior surface of the base 55. The interface of the joint 214 along the tabs 212 may be canted, "S" shaped, or "C" shaped as shown, for example. Elsewhere along the perimeter, away from the tabs 212, in the area where the wall is milled down, the perimeter edge of the lens 65 is exposed as seen in FIG. 21D, to facilitate insertion and removal of the lens 65 by radial compression using forceps, for example.

Figure 22:
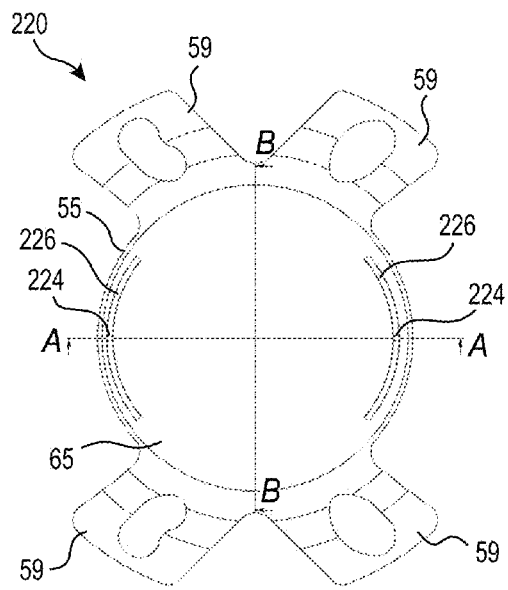
Figure 22B:
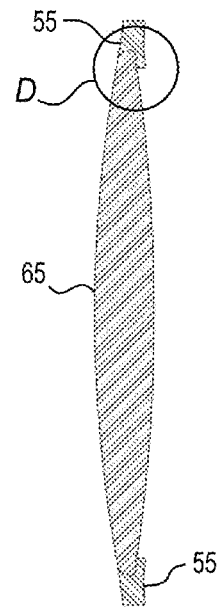
Figure 22A:
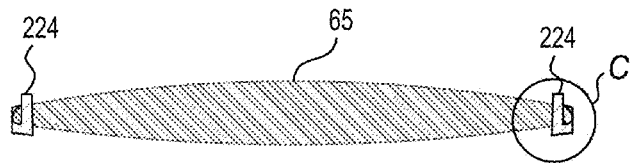
Figure 22C:
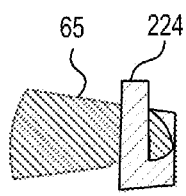
Figure 22D:
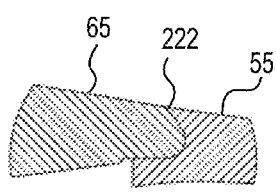

With reference to FIGS. 22-22D, an alternative modular IOL 220 is shown in front, sectional, and detailed views, respectively. FIG. 22A shows a cross-sectional view taken along line A-A in FIG. 22, FIG. 22B a cross-sectional view taken along line B-B in FIG. 22, FIG. 22C shows a detail view of circle C in FIG. 22A, and FIG. 22D shows a detail view of circle D in FIG. 22B. Modular IOL 220 includes a base 55 with associated haptics 59 and a lens 65. The base 55 includes a center hole such that the posterior optical surface of the lens 65 is not in contact with the base 55. The perimeter of the lens 65 is sized and shaped to fit in a circular recess formed in the base 55 to form a ledge on the base 55 and a flush joint 222. The flush joint 222 may be configured with an "S" shaped interface to securely connect the two components. A pair of pegs 224 extend anteriorly from the base 55 adjacent the inside perimeter thereof, and through a pair of arc-shaped slots 226 adjacent the perimeter of the lens 65. The arc-shaped slots may extend along a fraction of the circumference of the lens 65 as shown in FIG. 22. With this arrangement, the lens 65 may be selectively rotated relative to the base 55 for purposes of rotational adjustment in toric applications, for example.

The pegs 224 may be sized and configured to rise above the anterior surface of the lens 65 as shown in FIG. 22C. Forceps or the like may be inserted posteriorly through the arc-shaped slots 226 in the lens 65 to grasp the pegs 224 like a handle, followed by applying posterior pressure to the lens 65 while holding the pegs 224 stationary. By holding the pegs 224 and thus stabilizing the base 55 during connection of the lens 65 to the base 55, anterior-posterior forces applied to the capsular bag are reduced, thereby reducing the risk of capsular rupture.

Figure 23A:
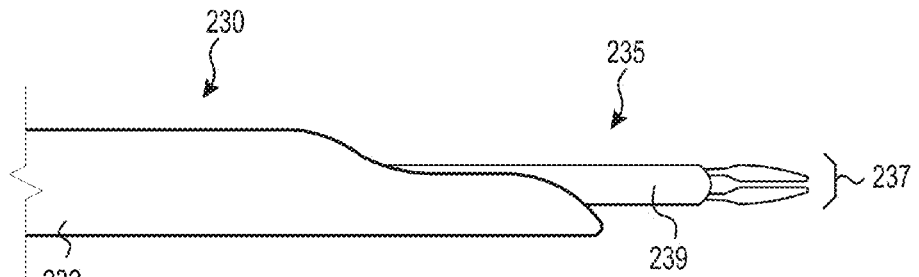
FIGS. 23A-23D are schematic illustrations of a lens removal system for a modular IOL according to an embodiment of the present disclosure.
Figure 23B:
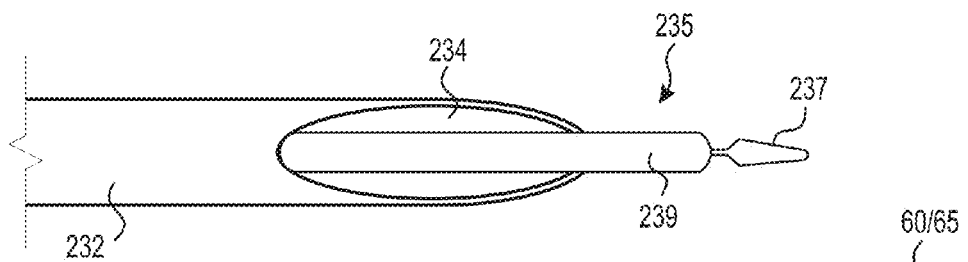
Figure 23C:
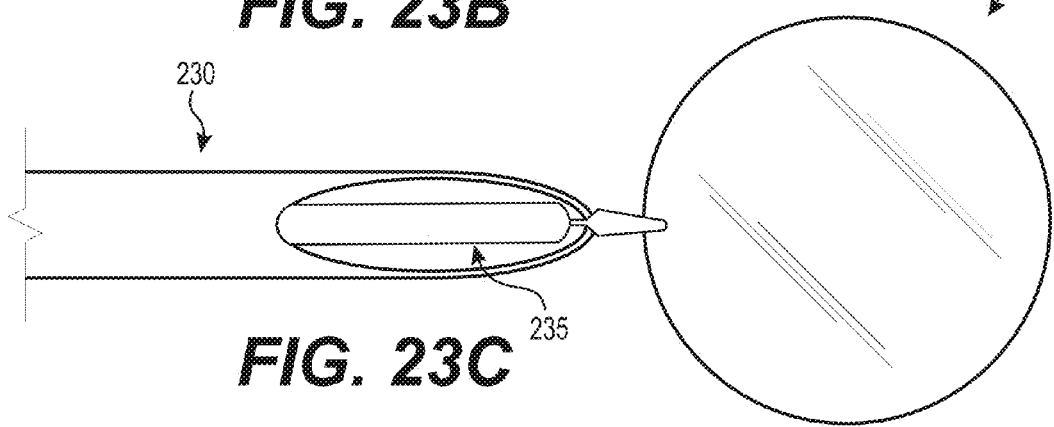
Figure 23D:
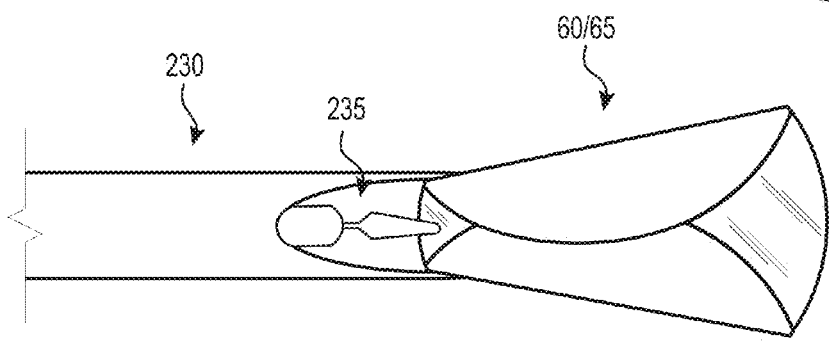

With reference FIGS. 23A-23D, a lens removal system for a modular IOL according to an embodiment of the present disclosure is shown schematically. FIGS. 23A and 23B are side and top views, respectively, of the lens removal system. FIGS. 23C and 23D are top views showing how the lens removal system may be used to remove lens 60/65. The lens removal or extractor system may include a cannula 230 and a pair of forceps 235. The cannula 230 may include a lumen sized to slidably receive the forceps 235. The cannula 230 may include a tubular shaft portion 232 and a contoured distal opening 234. The cannula 230 may be formed and configured similar to conventional IOL insertion devices, for example. The forceps 235 include a pair of atraumatic grasping tips 237 and a tubular shaft 239. The tubular shaft 239 may be advanced to compress the tips 237 and grasp the lens 60/65. The forceps 235 may be formed and configured similar to conventional ophthalmology forceps, for example, except that the tips 237 may be formed of or covered by a relatively soft polymeric material to avoid damage to the lens 60/65. Generally, any devices used to manipulate the modular IOL components described herein may be formed of or covered by a relatively soft polymeric material to avoid damage to the components thereof.

With reference to FIGS. 23C and 23D, the cannula 230 may be inserted through a corneal incision until its distal end is adjacent the capsulorhexis. The forceps 235 may be inserted into and through the cannula 230, until the distal tips 237 extend distally beyond the distal end of the cannula 230. The lens 60/65 to be extracted may be grasped with the forceps 235 as shown in FIG. 23C. With the lens 60/65 securely held by the forceps 235, the forceps 235 may be retracted proximally into the cannula 230. As the forceps 235 are retracted into the cannula 230, the lens 60/65 enters the contoured opening 234. The contoured opening 234 encourages the edges of the lens 60/65 to roll and fold as seen in FIG. 23D. Complete retraction of the forceps 235 into the cannula 230 thus captures the lens 60/65 safely in the lumen of the cannula 230 after which it may be removed from the eye. A similar approach may also be used to insert the lens 60/65, reversing the relevant steps.

Figure 24:
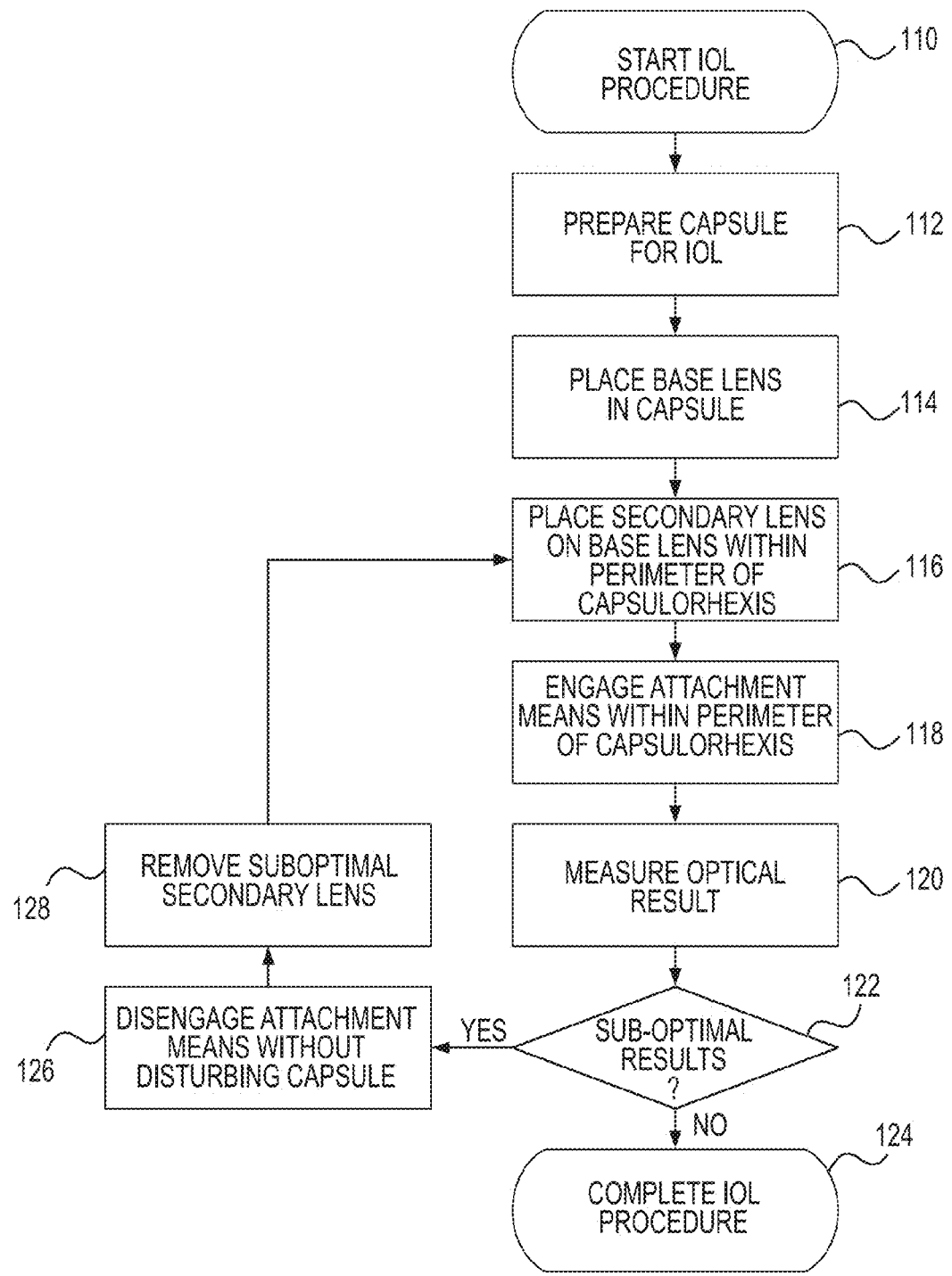
FIG. 24 is a schematic flow chart of a method for using a modular IOL, according to an embodiment of the present disclosure, wherein an exchange of the secondary lens is motivated by a sub-optimal optical result detected intra-operatively.
Figure 25:
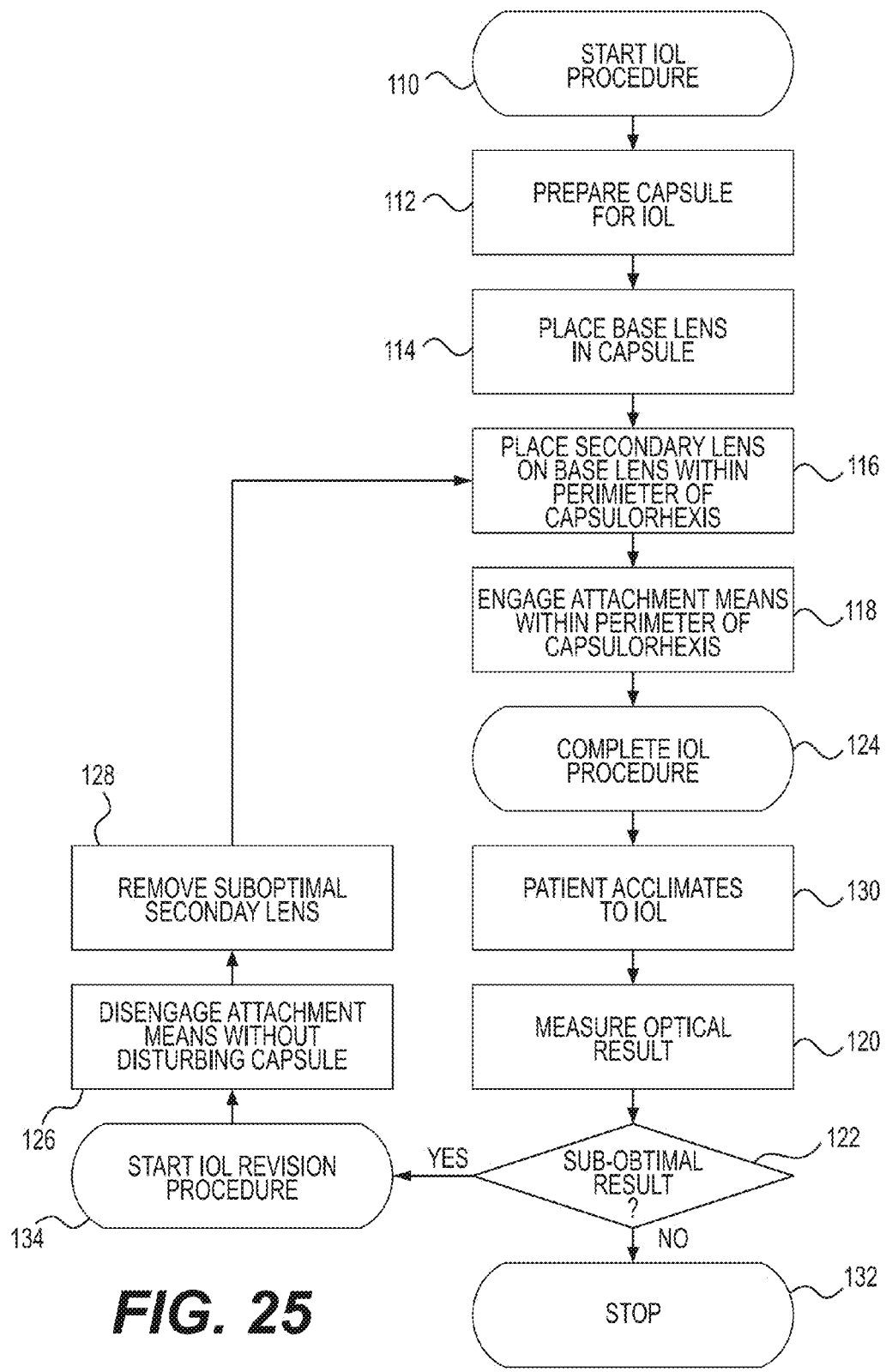
FIG. 25 is a schematic flow chart of a method for using a modular IOL, according to an embodiment of the present disclosure, wherein an exchange of the secondary lens is motivated by a sub-optimal optical result detected post-operatively.
Figure 26:
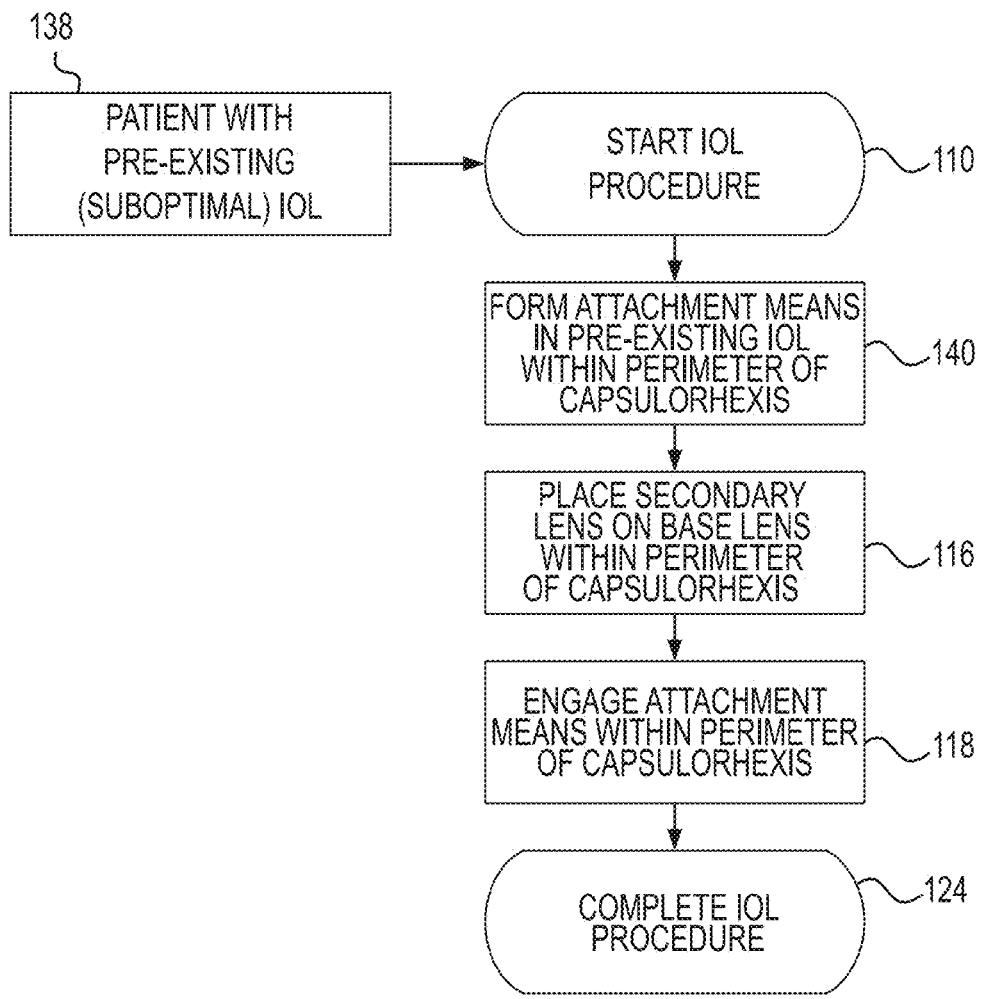
FIG. 26 is a schematic flow chart of a method for using a modular IOL, according to an embodiment of the present disclosure, wherein a secondary lens is attached to a primary lens by forming the attachment means in-situ.

FIGS. 24-26 describe example methods of using modular IOLs according to embodiments of the present disclosure. Although described with reference to a primary lens and a secondary lens by way of example, not necessarily limitation, the same or similar methods may be applied other modular IOL embodiments, including modular IOL embodiments described herein that comprise a base and a lens.

With reference to FIG. 24, a method for using a modular IOL according to an embodiment of the present disclosure is shown in a schematic flow chart. In this example, the secondary lens may be exchanged in the event of a sub-optimal optical result detected intra-operatively. An IOL implant procedure, such as cataract surgery, may be started 110 according to conventional practice. The native lens may then be prepared 112 to receive a modular IOL using conventional steps such as making corneal access incisions, cutting the capsulorhexis in the anterior capsular bag and removing the cataract lens by phacoemulsification. The base lens (i.e., primary lens 50) is then placed 114 in the lens capsule. The secondary lens (i.e., secondary lens 60) is then placed 116 on the base lens within the perimeter of the capsulorhexis without touching or otherwise disturbing the capsular bag. The attachment means is then engaged 118 to releasably connect the secondary lens to the base lens. Alternatively, the secondary lens may be attached to the base lens before placement in the lens capsule, such that the base lens and the secondary lens are inserted together as a unit. With both the base lens and the secondary lens in place, the optical result may be measured 120, for example by intra-operative aberrometry. The optical result may take into consideration refractive correction, centricity, toric correction, etc. A decision 122 is then made as to whether the optical result is optimal or sub-optimal. If the optical result is optimal or otherwise adequate, the IOL procedure is completed 124. However, if the optical result is sub-optimal or otherwise inadequate, the attachment means may be disengaged 126 and the secondary lens may be removed 128. A different secondary lens may be then placed 116 on the base lens, following the same subsequent steps as shown. The different secondary lens may have, for example, a different refractive power to correct refractive error, a different offset to correct for decentration, or a different toric power to correct for toric error.

With reference to FIG. 25, an alternative method for using a modular IOL according to an embodiment of the present disclosure is shown in a schematic flow chart. In this example, the secondary lens may be exchanged in the event of a sub-optimal optical result detected post-operatively. The same steps 110-118, and 124 may be performed as described previously, except that the patient is allowed to acclimate 130 to the modular IOL for a period of 1-4 weeks or more, for example. Upon a return visit, the optical result is measured 120 and a determination 122 is made as to whether the optical result is optimal or sub-optimal. If the optical result is optimal or otherwise adequate, the procedure is stopped 132. If the optical result is sub-optimal or otherwise inadequate, a revision procedure may be initiated 134 to replace the secondary lens following steps 126, 128, 116 and 118 as described previously.

This method allows the lens capsule to heal before deciding whether the optical result is sufficient, which may be advantageous to the extent the healing process alters the position of the primary and/or secondary lens. This method may also be applied on a chronic basis, where the optical needs or desires of the patient change over the course of a longer period of time (e.g., >1 year). In this example, the patient may require or desire a different correction such as a stronger refractive correction, a toric correction, or a multifocal correction, each of which may be addressed with a different secondary lens.

With reference to FIG. 26, another alternative method for using a modular IOL according to an embodiment of the present disclosure is shown in a schematic flow chart. In this example, the secondary lens may be implanted in a patient 138 having a pre-existing IOL that is optically sub-optimal or otherwise doesn't meet the needs and desires of the patient. After the procedure starts 110, an attachment mechanism may be formed in-situ in the pre-existing (base) IOL (step 140) using laser etching, for example, to form a groove as described previously. Formation of the groove may be performed within the perimeter of the previously cut capsulorhexis to avoid touching or otherwise disturbing the lens capsule. The secondary lens may then be placed 116 on the base lens within the perimeter of the capsulorhexis, and the attachment means may be engaged 118 to connect the secondary lens to the base lens, and the procedure may be completed 124 as described previously.

With reference to FIGS. 27-27D, an alternative modular IOL 270 is shown in front, sectional and detailed views, respectively. FIGS. 27A and 27B show cross-sectional views taken along line A-A and line B-B, respectively, in FIG. 27. FIGS. 27C and 27D show detail views of circle C in FIG. 27A and circle D FIG. 27B, respectively. Modular IOL 270 may be configured similar to modular IOL 210 shown in FIGS. 21-21D. Like modular IOL 210, modular IOL 270 includes a base 55 configured in the shape of an annulus or ring with a center opening and a recess defining a wall into which the correspondingly sized and shaped circular lens 65 may be placed. Also like modular IOL 210, the wall defining the recess extends along the inside perimeter of the base 55, with a portion thereof milled down to define two diametrically opposed tabs 272. The inside circumferential walls of the tabs 272 provide for a flush joint 274 as seen in FIG. 27C, such that the anterior surface of the lens 65 is flush with the anterior surface of the base 55. The interface of the joint 274 along the tabs 272 may be canted, "S" shaped, or "C" shaped as shown, for example. Elsewhere along the perimeter, away from the tabs 272, in the area where the wall is milled down, the perimeter edge of the lens 65 is exposed as seen in FIG. 27D, to facilitate insertion and removal of the lens 65 by radial compression using forceps, for example.

Because the base 55 includes a center opening that is devoid of material, the base 55 may have a larger outside optic diameter (excluding haptics) of approximately 8 mm, for example, and still be rolled into a delivery profile that is sufficiently small to fit through a corneal incision of less than approximately 2.4 mm, for example. This may allow at least a portion of the junction between the base 55 and lens 65 to be moved radially outward away from the circumferential perimeter of the capsulorhexis, which typically has a diameter of 5-6 mm. Moving at least a portion of the junction between the base 55 and the lens 65 radially outward from the perimeter of the capsulorhexis may reduce the amount of the junction that is in the field of view and thus reduce the potential for light scattering or optical aberrations (e.g., dysphotopsias) created thereby.

To further illustrate this advantage, consider a standard (single component) IOL, which typically has an optic diameter of conventional lenses is 6 mm. An IOL with a 6 mm diameter optic may be rolled and delivered through a 2.2 mm corneal incision. In order to secure the standard IOL in the capsular bag, the capsulorhexis is typically sized to allow the capsular bag to fully capture the standard IOL after the bag collapses and heals down. This drives surgeons to form a capsulorhexis having a diameter of approximately 4.5 mm to 5.5 mm.

Now consider IOL 270 by comparison. The modular (two piece) nature of IOL 270 and the hole in the base 55 allow both components (base 55 and lens 65) to be rolled and delivered through a small corneal incision (e.g., 2.2 mm), but don't require a capsulorhexis of 4.5 mm to 5.5 mm. Rather, because the base has a diameter of 8 mm (excluding haptics), the capsulorhexis diameter may be larger (e.g., 6.0 mm to 6.5 mm), which allows the lens 65 to comfortably fit inside the perimeter of the capsulorhexis and allows the junction 274 to be more peripheral to further minimize light scatter. Of course, notwithstanding these examples, any suitable dimensions may be selected to provide a gap between the lens 65 and the perimeter edge of the capsulorhexis in order to mitigate the need to manipulate the lens capsule to connect or disconnect the lens 65 to or from the base 55.

We claim:

1. A modular intraocular lens system for implantation in an eye, comprising:
   (a) an annular base having an inner perimeter defining a center hole and an outer perimeter with two or more haptics extending outwardly therefrom, the inner perimeter including a continuous circumferential recess having a ledge extending around an entirety of the inner perimeter, the continuous circumferential recess having an anterior rim and a posterior rim, wherein an inside diameter of the anterior rim is greater than an inside diameter of the posterior rim;
   (b) a lens disposed over the center hole in the continuous circumferential recess on the ledge of the annular base to form an overlapping joint between the lens and the annular base, wherein the joint is configured to permit insertion and removal of the lens to and from the annular base;
   (c) wherein the lens has an optical axis, and has a resting position along the optical axis relative to the annular base when disposed in the continuous circumferential recess; and
   (d) wherein the lens includes a pair of extensions disposed in the continuous circumferential recess that are configured to allow a change in rotational position of the lens relative to the annular base and maintain the resting position, and the pair of extensions comprises a pair of pegs, wherein the pair of pegs are disposed in a pair of holes in the annular base.

2. A modular intraocular lens system as in claim 1, wherein the annular base includes a series of holes disposed in the ledge of the continuous circumferential recess.

3. A modular intraocular lens system as in claim 1, wherein, in an implanted configuration, the intraocular lens system is configured to provide optical correction to the eye solely via an optic portion of the lens.

4. A modular intraocular lens system as in claim 1, wherein each of the extensions includes a radially-outer surface, and wherein the radially-outer surface of at least one of the extensions is curved.

5. A modular intraocular lens system as in claim 1, wherein the pair of extensions comprises a first extension and a second extension, and the first extension extends away from the second extension.

6. A modular intraocular lens system as in claim 5, wherein the first extension includes a peg of the pair of pegs, and the second extension includes a radially-outer edge of the lens.

7. A modular intraocular lens system as in claim 1, wherein at least one of the extensions is separated from a radially-outward-facing surface of the lens by a gap.

8. A modular intraocular lens system for implantation in an eye, comprising:
   (a) an annular base having an inner perimeter defining a center hole and an outer perimeter with two or more haptics extending outwardly therefrom, the inner perimeter including a continuous circumferential recess having a ledge extending around an entirety of the inner perimeter, the continuous circumferential recess having an anterior rim and a posterior rim, wherein an inside diameter of the anterior rim is greater than an inside diameter of the posterior rim;
   (b) a lens having an optic portion and a curvilinear extension protruding away from the optic portion, the optic portion having an optical axis, and the optic portion disposed over the center hole and the curvilinear extension disposed in the continuous circumferential recess on the ledge of the annular base to form an overlapping joint, wherein the joint is configured to permit insertion and removal of the lens to and from the annular base, the lens also having a pair of extension members extending in a direction away from the curvilinear extension, wherein each of the pair of extension members extends from a different location on the curvilinear extension;
   (c) wherein the lens has a resting position along the optical axis relative to the annular base when disposed in the continuous circumferential recess; and
   (d) wherein the pair of extension members are configured to allow a change in rotational position of the lens relative to the annular base and maintain the resting position.

9. A modular intraocular lens system as in claim 8, wherein the overlapping joint comprises the anterior rim extending over and contacting an anterior portion of the curvilinear extension, and the posterior rim extending under and contacting a posterior portion of the curvilinear extension.

10. A modular intraocular lens system as in claim 8, wherein, in an implanted configuration, the intraocular lens system is configured to provide optical correction to the eye solely via the optic portion of the lens.

11. A modular intraocular lens system as in claim 8, wherein the curvilinear extension substantially surrounds the optic portion of the lens.

12. A modular intraocular lens system as in claim 8, wherein, in an implanted configuration, the optic portion of the lens is not in contact with the base.

13. A modular intraocular lens system as in claim 8, wherein the extension members are diametrically opposed on the curvilinear extension.

14. A modular intraocular lens system for implantation in an eye, comprising:
  (a) an annular base defining a through hole and including a plurality of haptics extending radially away from the annular base, the through hole being surrounded by a continuous circumferential recess, the continuous circumferential recess having an anterior rim portion and a posterior rim portion, wherein an inside diameter of the anterior rim portion is greater than an inside diameter of the posterior rim portion such that the posterior rim portion forms an anterior-facing posterior ledge extending around an entirety of the continuous circumferential recess;
  (b) a lens disposed over the hole, in the continuous circumferential recess, and on the anterior-facing posterior ledge to form an overlapping joint between the lens and the annular base, wherein the joint is configured to permit insertion and removal of the lens to and from the annular base;
  (c) wherein the lens has a resting position relative to at least one of an anterior end and a posterior end of the annular base when disposed in the continuous circumferential recess; and
  (d) wherein the lens includes a pair of extensions disposed in the continuous circumferential recess that are configured to allow rotation of the lens relative to the annular base from a first rotational position in which the lens is in the resting position to a second rotational position in which the lens is in the resting position, the second rotational position being different than the first rotational position.

15. A modular intraocular lens system as in claim 14, wherein the pair of extensions and the continuous circumferential recess are configured to facilitate rotation of the lens relative to the annular base through an angle of 360 degrees.

16. A modular intraocular lens system as in claim 14, wherein at least one of the extensions is spaced from a radially-outward-facing surface of the lens by a gap.

17. A modular intraocular lens system as in claim 14, wherein one of the extensions extends in a direction away from the other of the extensions.

18. A modular intraocular lens system as in claim 17, wherein at least one of the extensions extends radially outwardly.

19. A modular intraocular lens system as in claim 14, wherein the extensions are diametrically opposed on the lens.

20. A modular intraocular lens system as in claim 14, wherein at least one of the extensions includes a fixed end and a free end opposite the fixed end.

21. A modular intraocular lens system as in claim 14, wherein at least one of the extensions includes a planar posterior surface and a curvilinear lateral surface.

22. A modular intraocular lens system for implantation in an eye having a visual axis, comprising:
  (a) an annular base defining a center through hole and including a plurality of haptics extending from the annular base, the center through hole being surrounded by a continuous circumferential recess, the continuous circumferential recess having an anterior rim portion and a posterior rim portion, wherein an inside diameter of the anterior rim portion is greater than an inside diameter of the posterior rim portion to form a posterior ledge extending around an entirety of the continuous circumferential recess;
  (b) a lens disposed over the hole, in the recess, and on the posterior ledge of the annular base to form an overlapping joint between the lens and the annular base, wherein the joint is configured to (i) permit insertion and removal of the lens to and from the annular base, (ii) permit adjustment of a position of the lens relative to the base around the visual axis, and (iii) limit movement of the lens relative to the base along the visual axis;
  (c) wherein the lens includes a pair of opposing protrusions disposed in the recess that are configured to support the lens on the posterior ledge while allowing an adjustment in rotational position of the lens relative to the base.

23. A modular intraocular lens system as in claim 22, wherein at least one of the protrusions is spaced from a radially-outward-facing surface of the lens by a gap.

24. A modular intraocular lens system as in claim 22, wherein the pair of opposing protrusions extend from diametrically opposed portions of the lens.

25. A modular intraocular lens system as in claim 22, wherein at least one of the protrusions includes a planar posterior surface and a curvilinear lateral surface.

26. A modular intraocular lens system as in claim 22, wherein at least one of the protrusions has a fixed end and a free end opposite the fixed end.

27. A modular intraocular lens system as in claim 26, wherein the free end engages the annular base.

28. A modular intraocular lens system as in claim 22, wherein the pair of opposing protrusions engage spaced apart locations on the annular base.

* * * * *